(12) United States Patent
Modesitt

(10) Patent No.: US 8,241,325 B2
(45) Date of Patent: Aug. 14, 2012

(54) ACCESS AND CLOSURE DEVICE AND METHOD

(75) Inventor: D. Bruce Modesitt, San Carlos, CA (US)

(73) Assignee: Arstasis, Inc., Redwood City, CA (US)

(*) Notice: Subject to any disclaimer, the term of this patent is extended or adjusted under 35 U.S.C. 154(b) by 99 days.

(21) Appl. No.: 11/432,982

(22) Filed: May 12, 2006

(65) Prior Publication Data
US 2006/0271078 A1 Nov. 30, 2006

Related U.S. Application Data

(60) Provisional application No. 60/680,388, filed on May 12, 2005.

(51) Int. Cl.
*A61B 17/08* (2006.01)
(52) U.S. Cl. .......................... 606/215; 606/213
(58) Field of Classification Search .................. 606/167, 606/213, 215, 216, 221; 604/164.01, 11, 604/158, 115
See application file for complete search history.

(56) References Cited

U.S. PATENT DOCUMENTS

| | | |
|---|---|---|
| 2,857,925 A | 6/1955 | Higginbotham |
| 3,727,614 A | 4/1973 | Kniazuk |
| 3,730,185 A | 5/1973 | Cook et al. |
| 4,006,747 A | 2/1977 | Kronenthal et al. |
| 4,744,364 A | 5/1988 | Kensey |
| 4,774,949 A | 10/1988 | Fogarty |
| 4,850,960 A | 7/1989 | Grayzel |
| 4,890,611 A | 1/1990 | Monfort et al. |
| 4,921,484 A | 5/1990 | Hillstead |
| 4,955,897 A | 9/1990 | Ship |
| 4,962,755 A * | 10/1990 | King et al. .......................... 601/2 |
| 5,183,464 A | 2/1993 | Dubrul et al. |
| 5,271,415 A | 12/1993 | Foerster et al. |
| 5,304,184 A | 4/1994 | Hathaway et al. |
| 5,336,221 A | 8/1994 | Anderson |
| 5,358,507 A | 10/1994 | Daily |
| 5,364,359 A | 11/1994 | van den Haak |
| 5,364,389 A * | 11/1994 | Anderson .......................... 606/8 |
| 5,368,601 A | 11/1994 | Sauer et al. |
| 5,380,290 A | 1/1995 | Makower et al. |
| 5,383,897 A | 1/1995 | Wholey |

(Continued)

FOREIGN PATENT DOCUMENTS
EP 0637431 2/1995
(Continued)

OTHER PUBLICATIONS

Franklin, I.J. et al. (1999). "Uptake of Tetracycline by Aortic Aneurysm Wall and Its Effect on Inflammation and Proteolysis," *Brit. J. Surgery* 86(6):771-775.

(Continued)

*Primary Examiner* — Corrine M McDermott
*Assistant Examiner* — Melissa Ryckman
(74) *Attorney, Agent, or Firm* — Vista IP Law Group LLP

(57) ABSTRACT

Devices and methods for accessing and closing vascular sites are disclosed. Self-sealing closure devices and methods are disclosed. A device that can make both steeply sloping and flat access paths into a vascular lumen is disclosed. The device can also form arteriotomies with sections cleaved between a vessel's intima and adventitia. Methods for using the device are also disclosed.

15 Claims, 28 Drawing Sheets

U.S. PATENT DOCUMENTS

| | | | |
|---|---|---|---|
| 5,391,182 A | 2/1995 | Chin | |
| 5,391,183 A | 2/1995 | Janzen et al. | |
| 5,403,329 A | 4/1995 | Hinchcliffe | |
| 5,415,657 A | 5/1995 | Taymor-Luria | |
| 5,417,699 A | 5/1995 | Klein et al. | |
| 5,437,665 A | 8/1995 | Munro | |
| 5,439,469 A | 8/1995 | Heaven et al. | |
| 5,451,230 A | 9/1995 | Steinert | |
| 5,462,561 A | 10/1995 | Voda | |
| 5,467,786 A | 11/1995 | Allen et al. | |
| 5,470,338 A | 11/1995 | Whitfield et al. | |
| 5,474,568 A | 12/1995 | Scott | |
| 5,476,470 A | 12/1995 | Fitzgibbons, Jr. | |
| 5,489,288 A | 2/1996 | Buelna | |
| 5,496,332 A | 3/1996 | Sierra et al. | |
| 5,496,334 A | 3/1996 | Klundt et al. | |
| 5,503,634 A | 4/1996 | Christy | |
| 5,507,744 A | 4/1996 | Tay et al. | |
| 5,527,321 A | 6/1996 | Hinchliffe | |
| 5,527,322 A | 6/1996 | Klein et al. | |
| 5,536,255 A | 7/1996 | Moss | |
| 5,571,169 A | 11/1996 | Plaia et al. | |
| 5,613,974 A | 3/1997 | Andreas et al. | |
| 5,620,461 A | 4/1997 | Muijs Van De Moer et al. | |
| 5,622,188 A | 4/1997 | Plaia et al. | |
| 5,645,566 A | 7/1997 | Brenneman et al. | |
| 5,653,717 A | 8/1997 | Ko et al. | |
| 5,695,504 A | 12/1997 | Gifford, III et al. | |
| 5,700,273 A | 12/1997 | Buelna et al. | |
| 5,709,224 A | 1/1998 | Behl et al. | |
| 5,746,755 A | 5/1998 | Wood et al. | |
| 5,762,066 A | 6/1998 | Law et al. | |
| 5,766,183 A | 6/1998 | Sauer | |
| 5,772,673 A | 6/1998 | Cuny et al. | |
| 5,779,719 A | 7/1998 | Klein et al. | |
| 5,792,152 A | 8/1998 | Klein et al. | |
| 5,797,929 A | 8/1998 | Andreas et al. | |
| 5,810,810 A | 9/1998 | Tay et al. | |
| 5,817,108 A | 10/1998 | Poncet | |
| 5,830,232 A | 11/1998 | Hasson | |
| 5,836,955 A | 11/1998 | Buelna et al. | |
| 5,846,253 A | 12/1998 | Buelna et al. | |
| 5,860,990 A | 1/1999 | Nobles et al. | |
| 5,860,991 A | 1/1999 | Klein et al. | |
| 5,868,762 A | 2/1999 | Cragg et al. | |
| 5,882,302 A | 3/1999 | Driscoll, Jr. et al. | |
| 5,902,311 A | 5/1999 | Andreas et al. | |
| 5,921,994 A | 7/1999 | Andreas et al. | |
| 5,941,897 A | 8/1999 | Myers | |
| 5,954,732 A | 9/1999 | Hart et al. | |
| 5,972,005 A | 10/1999 | Stalker et al. | |
| 5,972,013 A | 10/1999 | Schmidt | |
| 5,980,539 A | 11/1999 | Kontos | |
| 5,984,917 A | 11/1999 | Fleischman et al. | |
| 5,984,948 A | 11/1999 | Hasson | |
| 5,984,950 A | 11/1999 | Cragg et al. | |
| 6,033,401 A | 3/2000 | Edwards et al. | |
| 6,036,699 A | 3/2000 | Andreas et al. | |
| 6,036,721 A | 3/2000 | Harren et al. | |
| 6,042,601 A | 3/2000 | Smith | |
| 6,063,085 A | 5/2000 | Tay et al. | |
| 6,071,292 A | 6/2000 | Makower et al. | |
| 6,071,300 A | 6/2000 | Brenneman et al. | |
| 6,077,276 A | 6/2000 | Kontos | |
| 6,080,175 A | 6/2000 | Hogendijk | |
| 6,093,173 A | 7/2000 | Balceta et al. | |
| 6,117,144 A | 9/2000 | Nobles et al. | |
| 6,117,145 A | 9/2000 | Wood et al. | |
| 6,136,010 A * | 10/2000 | Modesitt et al. | 606/144 |
| 6,139,560 A | 10/2000 | Kremer | |
| 6,143,004 A | 11/2000 | Davis et al. | |
| 6,146,397 A | 11/2000 | Harkrider, Jr. | |
| 6,152,918 A * | 11/2000 | Padilla et al. | 606/15 |
| 6,159,232 A | 12/2000 | Nowakowski | |
| 6,171,317 B1 | 1/2001 | Jackson et al. | |
| 6,179,832 B1 | 1/2001 | Jones et al. | |
| 6,190,396 B1 | 2/2001 | Whitin et al. | |
| 6,197,042 B1 | 3/2001 | Ginn et al. | |
| 6,203,554 B1 | 3/2001 | Roberts | |
| 6,206,893 B1 | 3/2001 | Klein et al. | |
| 6,206,895 B1 | 3/2001 | Levinson | |
| 6,245,079 B1 | 6/2001 | Nobles et al. | |
| 6,258,084 B1 | 7/2001 | Goldman et al. | |
| 6,302,898 B1 | 10/2001 | Edwards et al. | |
| 6,358,244 B1 | 3/2002 | Newman et al. | |
| 6,358,556 B1 | 3/2002 | Ding et al. | |
| 6,371,975 B2 | 4/2002 | Cruise et al. | |
| 6,383,208 B1 | 5/2002 | Sancoff et al. | |
| 6,395,015 B1 | 5/2002 | Borst et al. | |
| 6,398,782 B1 | 6/2002 | Pecor et al. | |
| 6,454,777 B1 | 9/2002 | Green | |
| 6,457,182 B1 | 10/2002 | Szczesuil et al. | |
| 6,458,147 B1 | 10/2002 | Cruise et al. | |
| 6,468,228 B1 * | 10/2002 | Topel et al. | 600/567 |
| 6,475,182 B1 | 11/2002 | Hnojewyj et al. | |
| 6,506,210 B1 | 1/2003 | Kanner | |
| 6,517,553 B2 | 2/2003 | Klein et al. | |
| 6,524,321 B2 | 2/2003 | Kanesaka | |
| 6,524,326 B1 | 2/2003 | Zhu et al. | |
| 6,533,795 B1 | 3/2003 | Tran et al. | |
| 6,562,059 B2 * | 5/2003 | Edwards et al. | 606/213 |
| 6,565,583 B1 | 5/2003 | Deaton et al. | |
| 6,569,012 B2 | 5/2003 | Lydon et al. | |
| 6,623,510 B2 | 9/2003 | Carley et al. | |
| 6,626,855 B1 | 9/2003 | Weng et al. | |
| 6,641,592 B1 | 11/2003 | Sauer et al. | |
| 6,656,136 B1 | 12/2003 | Weng et al. | |
| 6,663,655 B2 | 12/2003 | Ginn et al. | |
| 6,676,685 B2 | 1/2004 | Pedros et al. | |
| 6,682,489 B2 | 1/2004 | Tenerz et al. | |
| 6,689,152 B2 | 2/2004 | Balceta et al. | |
| 6,719,694 B2 | 4/2004 | Weng et al. | |
| 6,719,750 B2 | 4/2004 | Varner et al. | |
| 6,733,515 B1 | 5/2004 | Edwards et al. | |
| 6,743,195 B2 | 6/2004 | Zucker | |
| 6,749,621 B2 | 6/2004 | Pantages et al. | |
| 6,749,622 B2 | 6/2004 | McGuckin, Jr. et al. | |
| 6,767,356 B2 | 7/2004 | Kanner et al. | |
| 6,773,699 B1 | 8/2004 | Soltz et al. | |
| 6,780,197 B2 | 8/2004 | Roe et al. | |
| 6,790,220 B2 | 9/2004 | Morris et al. | |
| 6,802,822 B1 | 10/2004 | Dodge | |
| 6,818,008 B1 | 11/2004 | Cates et al. | |
| 6,840,952 B2 | 1/2005 | Saker et al. | |
| 6,843,792 B2 | 1/2005 | Nishtala et al. | |
| 6,846,319 B2 | 1/2005 | Ginn et al. | |
| 6,846,320 B2 | 1/2005 | Ashby et al. | |
| 6,846,321 B2 | 1/2005 | Zucker | |
| 6,860,895 B1 | 3/2005 | Akerfeldt et al. | |
| 6,863,680 B2 | 3/2005 | Ashby | |
| 6,890,342 B2 | 5/2005 | Zhu et al. | |
| 6,890,343 B2 | 5/2005 | Ginn et al. | |
| 6,890,344 B2 | 5/2005 | Levinson | |
| 6,893,431 B2 | 5/2005 | Naimark et al. | |
| 6,896,692 B2 | 5/2005 | Ginn et al. | |
| 6,918,890 B2 | 7/2005 | Schmidt | |
| 6,929,655 B2 | 8/2005 | Egnelöv et al. | |
| 6,936,053 B1 | 8/2005 | Weiss | |
| 6,939,348 B2 | 9/2005 | Malecki et al. | |
| 6,939,357 B2 | 9/2005 | Navarro et al. | |
| 6,939,363 B2 | 9/2005 | Akerfeldt | |
| 6,939,364 B1 | 9/2005 | Soltz et al. | |
| 6,942,674 B2 | 9/2005 | Belef et al. | |
| 6,949,080 B2 | 9/2005 | Wolf et al. | |
| 6,949,107 B2 | 9/2005 | McGuckin, Jr. et al. | |
| 6,949,114 B2 | 9/2005 | Milo et al. | |
| 6,964,668 B2 | 11/2005 | Modesitt et al. | |
| 6,969,397 B2 | 11/2005 | Ginn | |
| 6,981,983 B1 | 1/2006 | Rosenblatt et al. | |
| 6,994,686 B2 | 2/2006 | Cruise et al. | |
| 7,001,400 B1 | 2/2006 | Modesitt et al. | |
| 7,008,440 B2 | 3/2006 | Sing et al. | |
| 7,008,442 B2 | 3/2006 | Brightbill | |
| 7,025,746 B2 | 4/2006 | Tal | |
| 7,025,776 B1 | 4/2006 | Houser et al. | |
| 7,029,489 B1 | 4/2006 | Ashby et al. | |
| 7,037,322 B1 | 5/2006 | Sing et al. | |

| | | |
|---|---|---|
| 7,037,323 B2 | 5/2006 | Sing et al. |
| 7,041,119 B2 | 5/2006 | Green |
| 7,074,232 B2 | 7/2006 | Kanner et al. |
| 7,077,848 B1 | 7/2006 | de Juan, Jr. et al. |
| 7,081,125 B2 | 7/2006 | Edwards et al. |
| 7,083,628 B2 | 8/2006 | Bachmen |
| 7,141,055 B2 | 11/2006 | Abrams et al. |
| 7,175,646 B2 | 2/2007 | Brenneman |
| 7,179,270 B2 | 2/2007 | Makower |
| 7,182,763 B2 | 2/2007 | Nardella |
| 7,186,251 B2 | 3/2007 | Malecki et al. |
| 7,226,467 B2 | 6/2007 | Lucatero et al. |
| 7,235,087 B2 | 6/2007 | Modesitt et al. |
| 7,247,162 B1 | 7/2007 | Thornton |
| 7,250,028 B2 | 7/2007 | Julian et al. |
| 7,279,001 B2 | 10/2007 | Addis et al. |
| 7,291,159 B2 | 11/2007 | Schmelzeisen-Redeker et al. |
| 7,316,704 B2 | 1/2008 | Bagaoisan et al. |
| 7,322,976 B2 | 1/2008 | Yassinzadeh |
| 7,335,220 B2 | 2/2008 | Khosravi et al. |
| 7,361,180 B2 | 4/2008 | Saadat et al. |
| 7,361,183 B2 | 4/2008 | Ginn |
| 7,377,927 B2 | 5/2008 | Burdulis et al. |
| 7,381,210 B2 | 6/2008 | Zarbatany et al. |
| 7,390,328 B2 | 6/2008 | Modesitt |
| 7,390,329 B2 | 6/2008 | Westra et al. |
| 7,470,237 B2 | 12/2008 | Beckman et al. |
| 7,494,460 B2 | 2/2009 | Haarstad et al. |
| 7,572,274 B2 | 8/2009 | Yassinzadeh |
| 7,597,705 B2 | 10/2009 | Forsberg et al. |
| 7,609,673 B2 | 10/2009 | Bergenlid et al. |
| 7,621,925 B2 | 11/2009 | Saadat et al. |
| 7,621,936 B2 | 11/2009 | Cragg et al. |
| 7,635,329 B2 | 12/2009 | Goldfarb et al. |
| 7,662,128 B2 | 2/2010 | Salcudean et al. |
| 7,678,133 B2 | 3/2010 | Modesitt |
| 7,704,261 B2 | 4/2010 | Sakamoto et al. |
| 7,704,264 B2 | 4/2010 | Ewers et al. |
| 7,736,347 B2 | 6/2010 | Kaplan et al. |
| 7,762,977 B2 | 7/2010 | Porter et al. |
| 7,837,696 B2 | 11/2010 | Modesitt et al. |
| 7,842,047 B2 | 11/2010 | Modesitt et al. |
| 7,846,170 B2 | 12/2010 | Modesitt et al. |
| 7,850,654 B2 | 12/2010 | Belhe et al. |
| 7,850,701 B2 | 12/2010 | Modesitt et al. |
| 7,867,249 B2 | 1/2011 | Palermo et al. |
| 7,875,052 B2 | 1/2011 | Kawaura et al. |
| 2001/0031922 A1 | 10/2001 | Weng et al. |
| 2001/0047165 A1 | 11/2001 | Makower et al. |
| 2002/0016614 A1 | 2/2002 | Klein et al. |
| 2002/0062146 A1 | 5/2002 | Makower et al. |
| 2002/0156495 A1 | 10/2002 | Brenneman et al. |
| 2003/0093093 A1 | 5/2003 | Modesitt et al. |
| 2003/0100921 A1 | 5/2003 | Addis et al. |
| 2003/0158578 A1* | 8/2003 | Pantages et al. ............ 606/213 |
| 2003/0233120 A1* | 12/2003 | Akerfeldt ............ 606/213 |
| 2003/0236542 A1 | 12/2003 | Makower |
| 2004/0044350 A1 | 3/2004 | Martin et al. |
| 2004/0086951 A1 | 5/2004 | Archakov et al. |
| 2004/0092964 A1 | 5/2004 | Modesitt et al. |
| 2004/0093024 A1 | 5/2004 | Lousararian et al. |
| 2004/0097978 A1 | 5/2004 | Modesitt et al. |
| 2004/0122449 A1 | 6/2004 | Modesitt et al. |
| 2004/0138522 A1 | 7/2004 | Haarstad et al. |
| 2004/0143290 A1 | 7/2004 | Brightbill |
| 2004/0153123 A1 | 8/2004 | Palermo et al. |
| 2004/0158287 A1 | 8/2004 | Cragg et al. |
| 2004/0172058 A1 | 9/2004 | Edwards et al. |
| 2004/0176758 A1 | 9/2004 | Yassinzadeh et al. |
| 2004/0215232 A1 | 10/2004 | Belhe et al. |
| 2004/0220594 A1 | 11/2004 | de Canniere |
| 2004/0220604 A1 | 11/2004 | Fogarty et al. |
| 2004/0267307 A1 | 12/2004 | Bagaoisan et al. |
| 2004/0267308 A1 | 12/2004 | Bagaoisan et al. |
| 2005/0033361 A1 | 2/2005 | Galdonik et al. |
| 2005/0049634 A1 | 3/2005 | Chopra |
| 2005/0075653 A1 | 4/2005 | Saadat et al. |
| 2005/0085773 A1 | 4/2005 | Forsberg |
| 2005/0085851 A1 | 4/2005 | Fiehler et al. |
| 2005/0085852 A1 | 4/2005 | Ditter |
| 2005/0085854 A1* | 4/2005 | Ginn ............ 606/213 |
| 2005/0085855 A1 | 4/2005 | Forsberg |
| 2005/0085856 A1 | 4/2005 | Ginn |
| 2005/0090860 A1 | 4/2005 | Paprocki |
| 2005/0096697 A1 | 5/2005 | Forsberg et al. |
| 2005/0107826 A1 | 5/2005 | Zhu et al. |
| 2005/0125030 A1 | 6/2005 | Forsberg et al. |
| 2005/0143761 A1 | 6/2005 | Modesitt et al. |
| 2005/0149065 A1 | 7/2005 | Modesitt |
| 2005/0228443 A1 | 10/2005 | Yassinzadeh |
| 2005/0234507 A1 | 10/2005 | Geske et al. |
| 2005/0251189 A1 | 11/2005 | Saadat et al. |
| 2005/0267520 A1 | 12/2005 | Modesitt |
| 2005/0267522 A1 | 12/2005 | Yassinzadeh et al. |
| 2005/0277980 A1 | 12/2005 | Yassinzadeh |
| 2006/0009802 A1 | 1/2006 | Modesitt |
| 2006/0064159 A1 | 3/2006 | Porter et al. |
| 2006/0079914 A1 | 4/2006 | Modesitt et al. |
| 2006/0111741 A1 | 5/2006 | Nardella |
| 2006/0129101 A1 | 6/2006 | McGuckin, Jr. |
| 2006/0135990 A1 | 6/2006 | Johnson |
| 2006/0135991 A1 | 6/2006 | Kawaura et al. |
| 2006/0136035 A1 | 6/2006 | Hermann et al. |
| 2006/0142785 A1 | 6/2006 | Modesitt et al. |
| 2006/0167476 A1 | 7/2006 | Burdulis, Jr. et al. |
| 2006/0206125 A1 | 9/2006 | Fogarty et al. |
| 2006/0235449 A1 | 10/2006 | Schubart et al. |
| 2006/0259017 A1 | 11/2006 | Heil, Jr. |
| 2006/0264975 A1 | 11/2006 | Pipenhagen et al. |
| 2006/0271078 A1 | 11/2006 | Modesitt |
| 2007/0027454 A1 | 2/2007 | Modesitt |
| 2007/0027455 A1 | 2/2007 | Modesitt |
| 2007/0032802 A1 | 2/2007 | Modesitt |
| 2007/0032803 A1 | 2/2007 | Modesitt |
| 2007/0032804 A1 | 2/2007 | Modesitt |
| 2007/0106246 A1 | 5/2007 | Modesitt |
| 2007/0167959 A1 | 7/2007 | Modesitt et al. |
| 2007/0255313 A1 | 11/2007 | Modesitt |
| 2008/0097347 A1 | 4/2008 | Arvanaghi |
| 2009/0105744 A1 | 4/2009 | Modesitt et al. |
| 2009/0318889 A1 | 12/2009 | Modesitt |
| 2010/0016786 A1 | 1/2010 | Drews et al. |
| 2010/0016810 A1 | 1/2010 | Drews et al. |
| 2010/0125296 A1 | 5/2010 | Modesitt |

FOREIGN PATENT DOCUMENTS

| | | |
|---|---|---|
| EP | 1459691 | 9/2004 |
| WO | WO-03/082363 A1 | 10/2003 |
| WO | WO-2005/112791 A2 | 12/2005 |
| WO | WO-2006/017023 A2 | 2/2006 |
| WO | WO-2006/124896 A2 | 11/2006 |
| WO | WO 2008/042034 | 4/2008 |
| WO | WO 2008/070238 | 6/2008 |
| WO | WO 2008/097955 | 8/2008 |

OTHER PUBLICATIONS

Pyo, R. et al. (Jun. 2000). "Targeted Gene Disruption of Matrix Metalloproteinase-9 (Gelatinase B) Suppresses Development of Experimental Abdominal Aortic Aneurysms," *J. Clinical Investigation* 105(11):1641-1649.

Tambiah, J. et al. (2001). "Provocation of Experimental Aortic Inflammation and Dilatation by Inflammatory Mediators and *Chlamydia pneumoniae*," *Brit. J. Surgery* 88(7):935-940.

Walton, L.J. et al. (Jul. 6, 1999). "Inhibition of Prostaglandin $E_2$ Synthesis in Abdominal Aortic Aneurysms," *Circulation* 100:48-54.

Xu, Q. et al. (Aug. 11, 2000). "Sp1 Increases Expression of Cyclooxygenase-2 in Hypoxic Vascular Endothelium," *J. Biological Chemistry* 275(32):24583-24589.

International Search Report, mailed Aug. 20, 2007, for PCT Application No. PCT/US06/18915 filed on May 12, 2006, 2 pages.

Non-Final Office Action mailed Jul. 31, 2008, for U.S. Appl. No. 10/888,682, filed Jul. 10, 2004, 12 pages.

International Search Report mailed Aug. 8, 2008, for PCT Application No. PCT/US05/16623 filed May 12, 2005, three pages.

International Search Report mailed Jun. 5, 2008, for PCT Application No. PCT/US05/23107 filed Jun. 30, 2005, two pages.

Non-Final Office Action mailed Feb. 18, 2009, for U.S. Appl. No. 11/544,149, filed Oct. 6, 2006, 8 pages.
Non-Final Office Action mailed Feb. 18, 2009, for U.S. Appl. No. 11/545,272, filed Oct. 6, 2006, 7 pages.
Non-Final Office Action mailed Feb. 23, 2009, for U.S. Appl. No. 11/544,196, filed Oct. 6, 2006, 7 pages.
Non-Final Office Action mailed Feb. 23, 2009, for U.S. Appl. No. 11/544,365, filed Oct. 6, 2006, 6 pages.
Non-Final Office Action mailed Feb. 24, 2009, for U.S. Appl. No. 11/544,177, filed Oct. 6, 2006, 7 pages.
Non-Final Office Action mailed Jan. 9, 2009, for U.S. Appl. No. 11/544,317, filed Oct. 6, 2006, 11 pages.
Non-Final Office Action mailed Oct. 29, 2008, for U.S. Appl. No. 11/788,509, filed Apr. 19, 2007, eight pages.
Non-Final Office Action mailed Nov. 12, 2008, for U.S. Appl. No. 10/844,247, filed May 12, 2004, nine pages.
International Search Report mailed on Sep. 3, 2009, for PCT Application No. PCT/US2009/051317, filed on Jul. 21, 2009, three pages.
Invitation to Pay Additional Fees mailed on Sep. 10, 2009, for PCT Application No. PCT/US09/51320, filed on Jul. 21, 2009, two pages.
Written Opinion mailed on Aug. 20, 2007, for PCT Application No. PCT/US06/18915, filed on May 12, 2006, four pages.
Written Opinion mailed on Jun. 5, 2008, for PCT Application No. PCT/US05/23107, filed on Jun. 30, 2005, four pages.
Written Opinion mailed on Aug. 8, 2008, for PCT Application No. PCT/US05/16623, filed on May 12, 2005, three pages.
Written Opinion mailed on Sep. 3, 2009, for PCT Application No. PCT/US2009/051317, filed on Jul. 21, 2009, seven pages.
European Search Report mailed on Jun. 26, 2009, for EP Patent Application No. 08011884.7, filed on May 12, 2005, five pages.
Final Office Action mailed on Aug. 21, 2009, for U.S. Appl. No. 11/788,509, filed Apr. 19, 2007, ten pages.
Final Office Action mailed on Aug. 14, 2009, for U.S. Appl. No. 11/544,317, filed Oct. 6, 2006, eight pages.
Final Office Action mailed on Jul. 6, 2009, for U.S. Appl. No. 10/844,247, filed May 12, 2004, nine pages.
Final Office Action mailed on May 6, 2009, for U.S. Appl. No. 10/888,682, filed Jul. 10, 2004, eight pages.
Final Office Action mailed on Dec. 8, 2009, for U.S. Appl. No. 11/544,149, filed Oct. 6, 2006, 9 pages.
Final Office Action mailed on Nov. 27, 2009, for U.S. Appl. No. 11/544,196, filed Oct. 6, 2006, 6 pages.
Final Office Action mailed on Nov. 25, 2009, for U.S. Appl. No. 11/544,177, filed Oct. 6, 2006, 8 pages.
Final Office Action mailed on Nov. 25, 2009, for U.S. Appl. No. 11/545,272, filed Oct. 6, 2006, 6 pages.
Final Office Action mailed on Nov. 18, 2009, for U.S. Appl. No. 11/544,365, filed Oct. 6, 2006, 6 pages.
Notice of Allowance mailed on Nov. 3, 2009, for U.S. Appl. No. 10/888,682, filed Jul. 10, 2004, nine pages.
Non-final office action dated Mar. 28, 2011, for related U.S. Appl. No. 12/467,251, Inventor D. Bruce Modesitt, filed May 15, 2009, (11 pages).
Office action for related AU Patent Application No. 2006247355, dated Mar. 16, 2011, (16 pages).
PCT International Search Report and Written Opinion for PCT/US2011/020893, Applicant Arstasis, Inc., Forms PCT/ISA/210, 220, and 237, dated Apr. 19, 2011 (10 pages).
Final Office Action for related U.S. Appl. No. 11/873,957, Inventor D. Bruce Modesitt, filed Oct. 17, 2007, mailed May 4, 2011 (23 pages).
File history for related application U.S. Appl. No. 10/844,247, filed May 12, 2004, Inventor D. Bruce Modesitt, including (211 pages total): Amendment Response to Final Office Action mailed Jul. 6, 2009, for U.S. Appl. No. 10/844,247, submitted on Dec. 7, 2009; Examiner Interview Summary Record for U.S. Appl. No. 10/844,247, mailed Sep. 30, 2009; Final Office Action for U.S. Appl. No. 10/844,247, mailed Jul. 6, 2009; Applicant Arguments/Remarks Made in an Amendment in Response to Examiner Interview Summary Record mailed Mar. 24, 2009, for U.S. Appl. No. 10/844,247, submitted on Apr. 9, 2009; Examiner Interview Summary Record for U.S. Appl. No. 10/844,247, mailed Mar. 24, 2009; Amendment Response to Non Final Office Action mailed Nov. 12, 2008, for U.S. Appl. No. 10/844,247, submitted on Mar. 12, 2009; Non Final Office Action for U.S. Appl. No. 10/844,247, mailed Nov. 12, 2008; Response to Election/Restriction mailed Jun. 16, 2008 for U.S. Appl. No. 10/844,247, submitted on Jul. 16, 2008; Requirement for Restriction/Election for U.S. Appl. No. 10/844,247, mailed Jun. 16, 2008; Examiner Interview Summary Record for U.S. Appl. No. 10/844,247, mailed Oct. 9, 2007; Amendment Response to Final Office Action mailed Jun. 28, 2007, for U.S. Appl. No. 10/844,247, submitted on Sep. 27, 2007; Final Office Action for U.S. Appl. No. 10/844,247, mailed Jun. 28, 2007; Amendment Response to Non Final Office Action mailed Jan. 4, 2007, for U.S. Appl. No. 10/844,247, submitted on Apr. 4, 2007; Non Final Office Action for U.S. Appl. No. 10/844,247, mailed Jan. 4, 2007; Response to Election/Restriction mailed Sep. 28, 2006 for U.S. Appl. No. 10/844,247, submitted on Oct. 31, 2006; Requirement for Restriction/Election for U.S. Appl. No. 10/844,247, mailed Sep. 28, 2006; Application for U.S. Appl. No. 10/844,247, filed May 12, 2004.
File history for related application U.S. Appl. No. 11/544,196, filed Oct. 6, 2006, Inventor D. Bruce Modesitt, including (126 pages total): Terminal Disclaimer for U.S. Appl. No. 11/544,196, submitted Mar. 18, 2011; Amendment Response to Non Final Office Action mailed Jun. 23, 2010, for U.S. Appl. No. 11/544,196, submitted on Dec. 23, 2010; Examiner Interview Summary Record for U.S. Appl. No. 11/544,196, mailed Dec. 16, 2010; Non Final Office Action for U.S. Appl. No. 11/544,196, mailed Jun. 23, 2010; Amendment Response to Final Office Action mailed Nov. 27, 2009, for U.S. Appl. No. 11/544,196, submitted on May 7, 2010; Examiner Interview Summary Record for U.S. Appl. No. 11/544,196, mailed Feb. 16, 2010; Final Office Action for U.S. Appl. No. 11/544,196, mailed Nov. 27, 2009; Examiner Interview Summary Record for U.S. Appl. No. 11/544,196, mailed Aug. 6, 2009; Supplemental Amendment Response to Non Final Office Action mailed Sep. 2, 2003, for U.S. Appl. No. 11/544,196, submitted on Aug. 3, 2009; Amendment Response to Non Final Office Action mailed Sep. 2, 2003, for U.S. Appl. No. 11/544,196, submitted on Jun. 23, 2009; Non Final Office Action for U.S. Appl. No. 11/544,196, mailed Feb. 23, 2009; Preliminary Amendment for U.S. Appl. No. 11/544,196, submitted Oct. 6, 2006; Application for U.S. Appl. No. 11/544,196, filed Oct. 6, 2006.
File history for related application U.S. Appl. No. 11/545,272, filed Oct. 6, 2006, Inventor D. Bruce Modesitt, including (154 pages total): Terminal Disclaimer for U.S. Appl. No. 11/545,272, submitted Dec. 23, 2010; Amendment Response to Non Final Office Action mailed Jun. 23, 2010, for U.S. Appl. No. 11/545,272, submitted on Dec. 23, 2010; Examiner Interview Summary Record for U.S. Appl. No. 11/545,272, mailed Dec. 16, 2010; Non Final Office Action for U.S. Appl. No. 11/545,272, mailed Jun. 23, 2010; Amendment Response to Final Office Action mailed Nov. 25, 2009, for U.S. Appl. No. 11/545,272, submitted on May 7, 2010; Examiner Interview Summary Record for U.S. Appl. No. 11/545,272, mailed Feb. 16, 2010; Final Office Action for U.S. Appl. No. 11/545,272, mailed Nov. 25, 2009; Examiner Interview Summary Record for U.S. Appl. No. 11/545,272, mailed Aug. 3, 2009; Supplemental Amendment Response to Non Final Office Action mailed Feb. 18, 2009, for U.S. Appl. No. 11/545,272, submitted on Aug. 3, 2009; Amendment Response to Non Final Office Action mailed Feb. 18, 2009, for U.S. Appl. No. 11/545,272, submitted on Jun. 18, 2009; Non Final Office Action for U.S. Appl. No. 11/545,272, mailed Feb. 18, 2009; Preliminary Amendment for U.S. Appl. No. 11/545,272, submitted Oct. 6, 2006; Application for U.S. Appl. No. 11/545,272, filed Oct. 6, 2006.
File history for related application U.S. Appl. No. 11/544,365, filed Oct. 6, 2006, Inventor D. Bruce Modesitt, including (152 pages total): Terminal Disclaimer for U.S. Appl. No. 11/544,365, submitted Dec. 23, 2010; Amendment Response to Non Final Office Action mailed Jun. 25, 2010, for U.S. Appl. No. 11/544,365, submitted on Dec. 23, 2010; Examiner Interview Summary Record for U.S. Appl. No. 11/544,365, mailed Dec. 16, 2010; Non Final Office Action for U.S. Appl. No. 11/544,365, mailed Jun. 25, 2010; Amendment Response to Final Office Action mailed Nov. 18, 2009, for U.S. Appl. No. 11/544,365, submitted on May 7, 2010; Examiner Interview Summary Record for U.S. Appl. No. 11/544,365, mailed Feb. 16, 2010; Final Office Action for U.S. Appl. No. 11/544,365, mailed Nov. 18, 2009; Examiner Interview Summary Record for U.S. Appl. No. 11/544,365, mailed Aug. 6, 2009; Supplemental Amendment Response to Non Final Office Action mailed Feb. 23, 2009, for U.S. Appl. No. 11/544,365, submitted on Aug. 6, 2009; Amendment Response to Non Final Office Action mailed Feb. 23, 2009, for U.S. Appl. No. 11/544,365, submitted on Jun. 22, 2009; Non Final Office Action for U.S. Appl. No. 11/544,365, mailed Feb. 23, 2009; Preliminary Amendment for U.S. Appl. No. 11/544,365, submitted Oct. 6, 2006; Application for U.S. Appl. No. 11/544,365, filed Oct. 6, 2006.

File history for related application U.S. Appl. No. 11/544,177, filed Oct. 6, 2006, Inventor D. Bruce Modesitt, including (167 pages total): Terminal Disclaimer for U.S. Appl. No. 11/544,177, submitted Mar. 18, 2011; Amendment Response to Non Final Office Action mailed Jun. 22, 2010, for U.S. Appl. No. 11/544, 177, submitted on Dec. 22, 2010; Terminal Disclaimer for U.S. Appl. No. 11/544,177, submitted Dec. 22, 2011; Non Final Office Action for U.S. Appl. No. 11/544,177, mailed Jun. 22, 2010; Amendment Response to Final Office Action mailed Nov. 25, 2009, for U.S. Appl. No. 11/544,177, submitted on May 7, 2010; Examiner Interview Summary Record for U.S. Appl. No. 11/544,177, mailed Feb. 16, 2010; Final Office Action for U.S. Appl. No. 11/544,177, mailed Nov. 25, 2009; Examiner Interview Summary Record for U.S. Appl. No. 11/544,177, mailed Aug. 6, 2009; Supplemental Amendment Response to Non Final Office Action mailed Feb. 24, 2009, for U.S. Appl. No. 11/544,177, submitted on Aug. 6, 2009; Amendment Response to Non Final Office Action mailed Feb. 24, 2009, for U.S. Appl. No. 11/544,177, submitted on Jun. 24, 2009; Non Final Office Action for U.S. Appl. No. 11/544,177, mailed Feb. 24, 2009; Preliminary Amendment for U.S. Appl. No. 11/544,177, submitted Oct. 6, 2006; Application for U.S. Appl. No. 11/544,177, filed Oct. 6, 2006.

File history for related application U.S. Appl. No. 11/544,149, filed Oct. 6, 2006, Inventor D. Bruce Modesitt, including (170 pages total): Terminal Disclaimer for U.S. Appl. No. 11/544,149, submitted Mar. 18, 2011; Amendment Response to Non Final Office Action mailed Jun. 24, 2010, for U.S. Appl. No. 11/544,149, submitted on Dec. 23, 2010; Terminal Disclaimer for U.S. Appl. No. 11/544,149, submitted Dec. 23, 2011; Non Final Office Action for U.S. Appl. No. 11/544,149, mailed Jun. 24, 2010; Amendment Response to Final Office Action mailed Dec. 8, 2009, for U.S. Appl. No. 11/544,149, submitted on May 3, 2010; Examiner Interview Summary Record for U.S. Appl. No. 11/544,149, mailed Feb. 16, 2010; Final Office Action for U.S. Appl. No. 11/544,149, mailed Dec. 8, 2009; Examiner Interview Summary Record for U.S. Appl. No. 11/544,149, mailed Aug. 6, 2009; Supplemental Amendment Response to Non Final Office Action mailed Feb. 18, 2009, for U.S. Appl. No. 11/544,149, submitted on Aug. 6, 2009; Amendment Response to Non Final Office Action mailed Feb. 18, 2009, for U.S. Appl. No. 11/544,149, submitted on Jun. 18, 2009; Non Final Office Action for U.S. Appl. No. 11/544,149, mailed Feb. 18, 2009; Preliminary Amendment for U.S. Appl. No. 11/544,149, submitted Oct. 6, 2006; Application for U.S. Appl. No. 11/544,149, filed Oct. 6, 2006.

File history for related application U.S. Appl. No. 10/888,682, filed Jul. 10, 2004, Inventor D. Bruce Modesitt, including (141 pages total): Supplemental Amendment Response to Final Office Action mailed May 6, 2009 for U.S. Appl. No. 10/888,682, submitted on Aug. 28, 2009 Amendment Response to Final Office Action mailed May 6, 2009 for U.S. Appl. No. 10/888,682, submitted on Jul. 1, 2009 Final Office Action for U.S. Appl. No. 10/888,682, mailed May 6, 2009 Amendment Response to Non Final Office Action mailed Jul. 31, 2008 for U.S. Appl. No. 10/888,682, submitted on Nov. 26, 2008 Non Final Office Action for U.S. Appl. No. 10/888,682, mailed Jul. 31, 2008 Response to Restriction and Election mailed Feb. 15, 2008 for U.S. Appl. No. 10/888,682, submitted on Apr. 30, 2008 Requirement for Restriction and Election for U.S. Appl. No. 10/888,682, mailed on Feb. 15, 2008 Application for U.S. Appl. No. 10/888,682, filed Jul. 10, 2004.

File history for related application U.S. Appl. No. 12/693,395, filed Jan. 25, 2010, Inventor D. Bruce Modesitt, including (61 pages): Preliminary Amendment for U.S. Appl. No. 12/693,395, submitted on Jan. 25, 2010 Application for U.S. Appl. No. 12/693,395, filed Jan. 25, 2010.

File history for related application U.S. Appl. No. 11/544,317, filed Oct. 6, 2006, Inventor D. Bruce Modesitt, including (163 pages): Terminal Disclaimer Decision for U.S. Appl. No. 11/544,317, mailed on Mar. 15, 2011 Amendment Response to Non Final Office Action mailed Jun. 24, 2010 for U.S. Appl. No. 11/544,317, submitted on Dec. 23, 2010 Terminal Disclaimer for U.S. Appl. No. 11/544,317 as filed on Dec. 23, 2010 Non Final Office Action for U.S. Appl. No. 11/544,317, mailed Jun. 24, 2010 Amendment Response to Final Office Action mailed on Aug. 14, 2009 for U.S. Appl. No. 11/544,317, submitted on Feb. 12, 2010 Final Office Action for U.S. Appl. No. 11/544,317, mailed Aug. 14, 2009 Amendment Response to Non Final Office Action mailed Jan. 9, 2009 for U.S. Appl. No. 11/544,317, submitted on May 11, 2009 Non Final Office Action for U.S. Appl. No. 11/544,317, mailed Jan. 9, 2009 Amendment Response to Application filed on Oct. 6, 2006 for U.S. Appl. No. 11/544,317, submitted on Oct. 6, 2006 Application for U.S. Appl. No. 11/544,317, filed Oct. 6, 2006.

File history for related application U.S. Appl. No. 11/788,509, filed Apr. 19, 2007, Inventor D. Bruce Modesitt, including (288 pages): Terminal Disclaimer Decision for U.S. Appl. No. 11/788,509, mailed on Mar. 21, 2011 Terminal Disclaimer for U.S. Appl. No. 11/788,509, as filed on Mar. 18, 2011 Terminal Disclaimer Decision for U.S. Appl. No. 11/788,509, mailed on Mar. 11, 2011 Amendment Response to Non Final Office Action mailed Jun. 24, 2010 for U.S. Appl. No. 11/788,509, submitted on Dec. 23, 2010 Terminal Disclaimer for U.S. Appl. No. 11/788,509, as filed on Dec. 23, 2010 Non Final Office Action for U.S. Appl. No. 11/788,509, mailed Jun. 24, 2010 Supplemental Amendment Response to Final Office Action mailed Aug. 21, 2009 for U.S. Appl. No. 11/788,509, submitted on Apr. 29, 2010 Amendment Response to Final Office Action mailed Aug. 21, 2009 for U.S. Appl. No. 11/788,509, submitted on Feb. 19, 2010 Final Office Action for U.S. Appl. No. 11/788,509, mailed Aug. 21, 2009 Amendment Response to Notice Regarding Non-Responsive Amendment dated Apr. 15, 2009 for U.S. Appl. No. 11/788,509, submitted on May 14, 2009 Notice Regarding Non-Responsive Amendment for U.S. Appl. No. 11/788,509, dated Apr. 15, 2009 Amendment Response to Non Final Office Action mailed Oct. 29, 2008 for U.S. Appl. No. 11/788,509, submitted on Jan. 6, 2009 Non Final Office Action for U.S. Appl. No. 11/788,509, mailed Oct. 29, 2008 Response to PTO Notice to Applicant mailed May 15, 2007 for U.S. Appl. No. 11/788,509, submitted on Jul. 16, 2007 PTO Notice to Applicant for U.S. Appl. No. 11/788,509, mailed May 15, 2007 Amendment Response to Application as filed on Apr. 19, 2007 for U.S. Appl. No. 11/788,509, submitted on Apr. 19, 2007 Application for U.S. Appl. No. 11/788,509, filed Apr. 19, 2007.

File history for related application U.S. Appl. No. 12/467,251, filed May 15, 2009, Inventor D. Bruce Modesitt, including (46 pages): Amendment Response to Application as filed on May 15, 2009 for U.S. Appl. No. 12/467,251, submitted on May 15, 2009 Application for U.S. Appl. No. 12/467,251, filed May 15, 2009.

File history for related application U.S. Appl. No. 11/873,957, filed Oct. 17, 2007, Inventor D. Bruce Modesitt, et al., including (90 pages): Amendment Response to Notice Regarding Non-Responsive Amendment dated Feb. 7, 2011 for U.S. Appl. No. 11/873,957, submitted on Mar. 2, 2011 Examiner Interview Summary Record for U.S. Appl. No. 11/873,957, dated Feb. 7, 2011 Notice Regarding Non-Responsive Amendment for U.S. Appl. No. 11/873,957, dated Feb. 7, 2011 Amendment Response to Non Final Office Action mailed Aug. 2, 2010 for U.S. Appl. No. 11/873,957, submitted on Feb. 2, 2011 Terminal Disclaimer for U.S. Appl. No. 11/873,957, as filed on Feb. 2, 2011 Non Final Office Action for U.S. Appl. No. 11/873,957, mailed Aug. 2, 2010 Application for U.S. Appl. No. 11/873,957, filed Oct. 17, 2007.

File history for related application U.S. Appl. No. 12/507,038, filed Jul. 21, 2009, Inventor Michael Drews, et al., including (90 pages): Application for U.S. Appl. No. 12/507,038, filed Jul. 21, 2009.

File history for related application U.S. Appl. No. 12/507,043, filed Jul. 21, 2009, Inventor Michael Drews, et al., including (97 pages): Application for U.S. Appl. No. 12/507,043, filed Jul. 21, 2009.

File history for related application U.S. Appl. No. 12/780,768, filed May 14, 2010, Inventor Michael Drews, et al., including (97 pages): Application for U.S. Appl. No. 12/780,768, filed May 14, 2010.

File History for related U.S. Appl. No. 12/888,209, filed Sep. 22, 2010, Inventor D. Bruce Modesitt, et al., including (125 pages): Application for U.S. Appl. No. 12/888,309, filed Sep. 22, 2010.

File history for related application U.S. Appl. No. 13/004,848, filed Jan. 11, 2011, Inventor D. Bruce Modesitt, et al., including (91 pages): Application for U.S. Appl. No. 13/004,848, filed Jan. 11, 2011.

PCT International Preliminary Report on Patentability for PCT/US2005/016623, Applicant Arstasis, Inc., Forms PCT/IB/373 and PCT/ISA/237 dated Feb. 24, 2009. (4 pages).

PCT International Search Report and Written Opinion for PCT/US2005/016623, Applicant Arstasis, Inc., Forms PCT/ISA/210, 220, and 237 dated Aug. 8, 2008. (6 pages).

Office Action dated Apr. 13, 2010, for Australian Patent Application No. 2005244834, with a filing date of May 12, 2005. (3 pages).

Office Action dated Jun. 3, 2010, for Chinese Patent Application No. 200580023327.X, with a filing date of May 12, 2005, with English translation provided by Chinese associate. (7 pages).

Further Office Action dated Sep. 6, 2010, for Israeli Patent Application No. 179173, with a filing date of Jun. 30, 2005, with English translation provided by Israeli associate. (9 pages).

Response to Office Action submitted Jul. 13, 2010, for Israeli Patent Application No. 179173, with a filing date of Jun. 30, 2005. (1 page).

Initial Office Action dated Jan. 25, 2010, for Israeli Patent Application No. 179173, with a filing date of Jun. 30, 2005, with English translation provided by Israeli associate. (5 pages).

Office Action dated Jan. 24, 2011, for Japanese Patent Application No. 2007-513356, with a filing date of May 12, 2005, and with English translation provided by Japanese associate, (7 pages).

Office Action dated Jan. 24, 2011, for Japanese Patent Application No. 2008-123950, with a filing date of May 12, 2005, and with English translation provided by Japanese associate, (4 pages).

PCT International Preliminary Report on Patentability for PCT/US2005/023107, Applicant Arstasis, Inc., Forms PCT/IB/373 and PCT/ISA/237 dated Mar. 3, 2009. (5 pages).

PCT International Search Report and Written Opinion for PCT/US2005/023107, Applicant Arstasis, Inc., Forms PCT/ISA/210 and 237 dated Jun. 5, 2008. (6 pages).

Office Action dated Jun. 4, 2010, for Australian Patent Application No. 2005272102, with a filing date of Jun. 30, 2005. (3 pages).

Response to Office Action submitted Oct. 18, 2010, for Chinese Patent Application No. 2005800293656, with English instructions to respond provided to Chinese associate, (27 pages).

Office Action dated Jun. 4, 2010, for Chinese Patent Application No. 2005800293656, with a filing date of Jun. 30, 2005, with English translation provided by Chinese associate. (10 pages).

Office Action dated Feb. 14, 2011, for European Patent Application No. 05787529.6, with a filing date of Jun. 30, 2005, (15 pages).

European Search Report from European Patent Office for EP application No. EP05787529.6, Applicant Arstasis, Inc., EPO Forms 1507, 1503, and P0459, dated Nov. 5, 2010. (5 pages).

Further Office Action dated May 24, 2010, for Israeli Patent Application No. 180497, with a filing date of May 12, 2005, with English translation provided by Israeli associate. (5 pages).

Response to Office Action submitted May 23, 2010, for Israeli Patent Application No. 180497, with a filing date of May 12, 2005, with English translation provided by Israeli associate. (7 pages).

Initial Office Action dated Jan. 24, 2010, for Israeli Patent Application No. 180497, with a filing date of May 12, 2005, with English translation provided by Israeli associate. (5 pages).

Office Action dated Dec. 8, 2010, for Japanese Patent Application No. 2007-0520363, with a filing date of Jun. 30, 2005, and with English translation provided by Japanese associate, (5 pages).

PCT International Search Report and Written Opinion for PCT/US2006/018915, Applicant Arstasis, Inc., Forms PCT/ISA/210 and 237 dated Aug. 20, 2007. (6 pages).

Response to Office Action submitted Nov. 6, 2010, for Chinese Patent Application No. 2006800252468, with English instructions to respond provided to Chinese associate. (29 pages).

Office Action dated May 22, 2009, for Chinese Patent Application No. 2006800252468, with a filing date of May 12, 2006, with English translation provided by Chinese associate. (7 pages).

PCT International Preliminary Report on Patentability for PCT/US2009/051320, Applicant Arstasis, Inc., Forms PCT/IB/373 and PCT/ISA/237 dated Jan. 25, 2011. (7 pages).

PCT International Search Report and Written Opinion for PCT/US2009/051320, Applicant Arstasis, Inc., Forms PCT/ISA/210, 220, and 237 dated Nov. 6, 2009. (11 pages).

PCT International Search Report and Written Opinion for PCT/US2010/035001, Applicant Arstasis, Inc., Forms PCT/ISA/210, 220, and 237 dated Jul. 19, 2010. (11 pages).

PCT International Search Report and Written Opinion for PCT/US2010/049859, Applicant Arstasis, Inc., Forms PCT/ISA/210, 220, and 237 dated Nov. 5, 2010. (14 pages).

\* cited by examiner

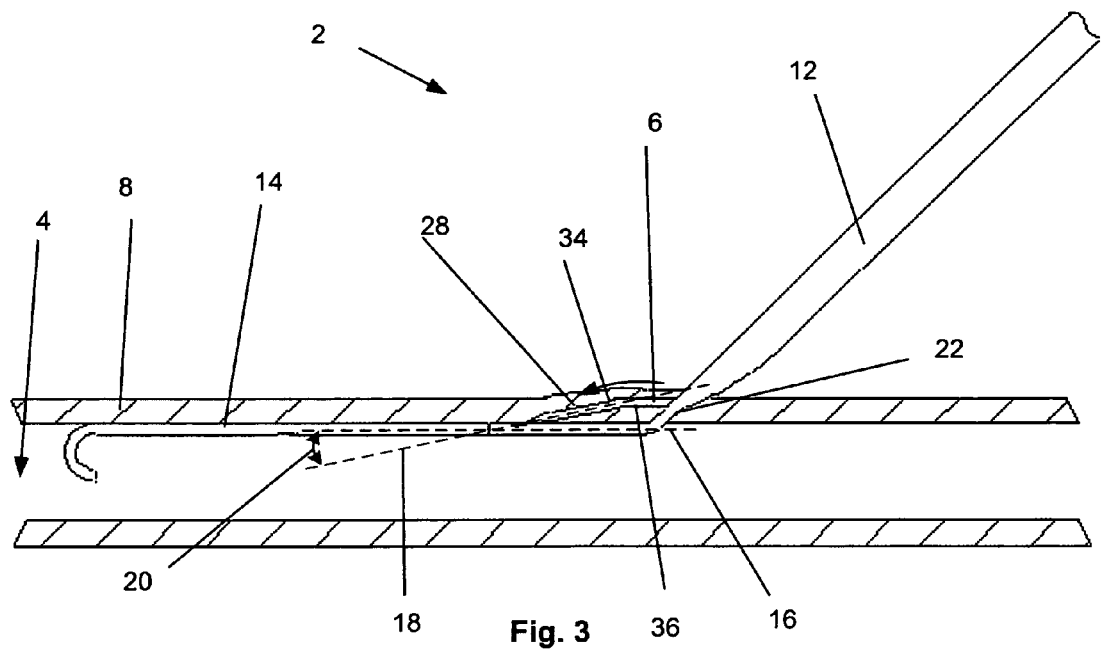
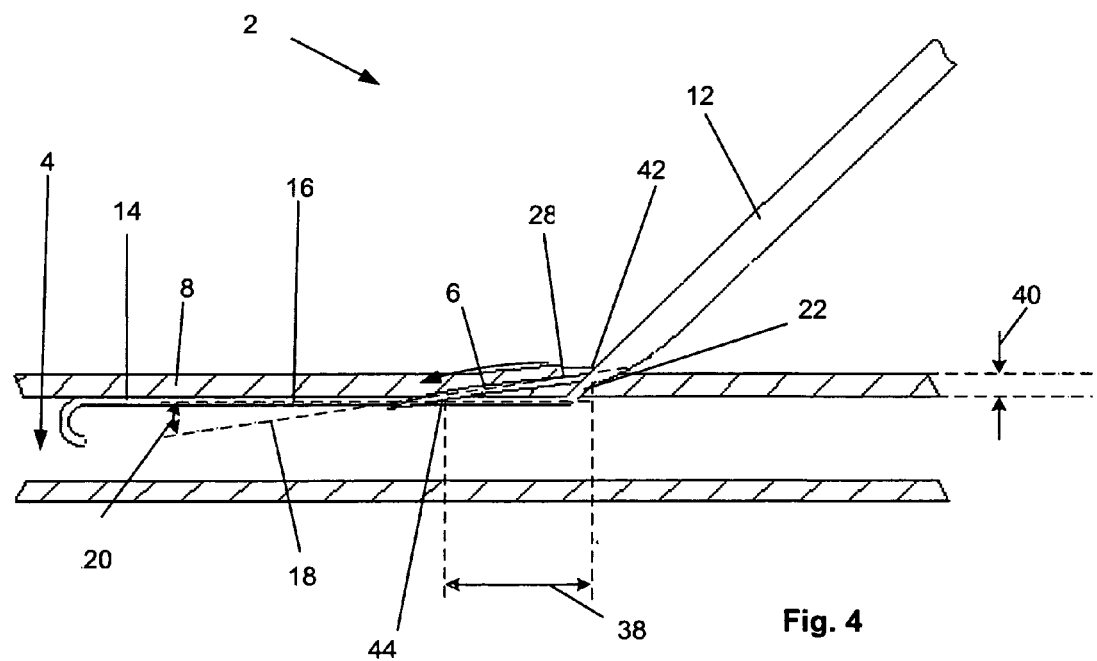

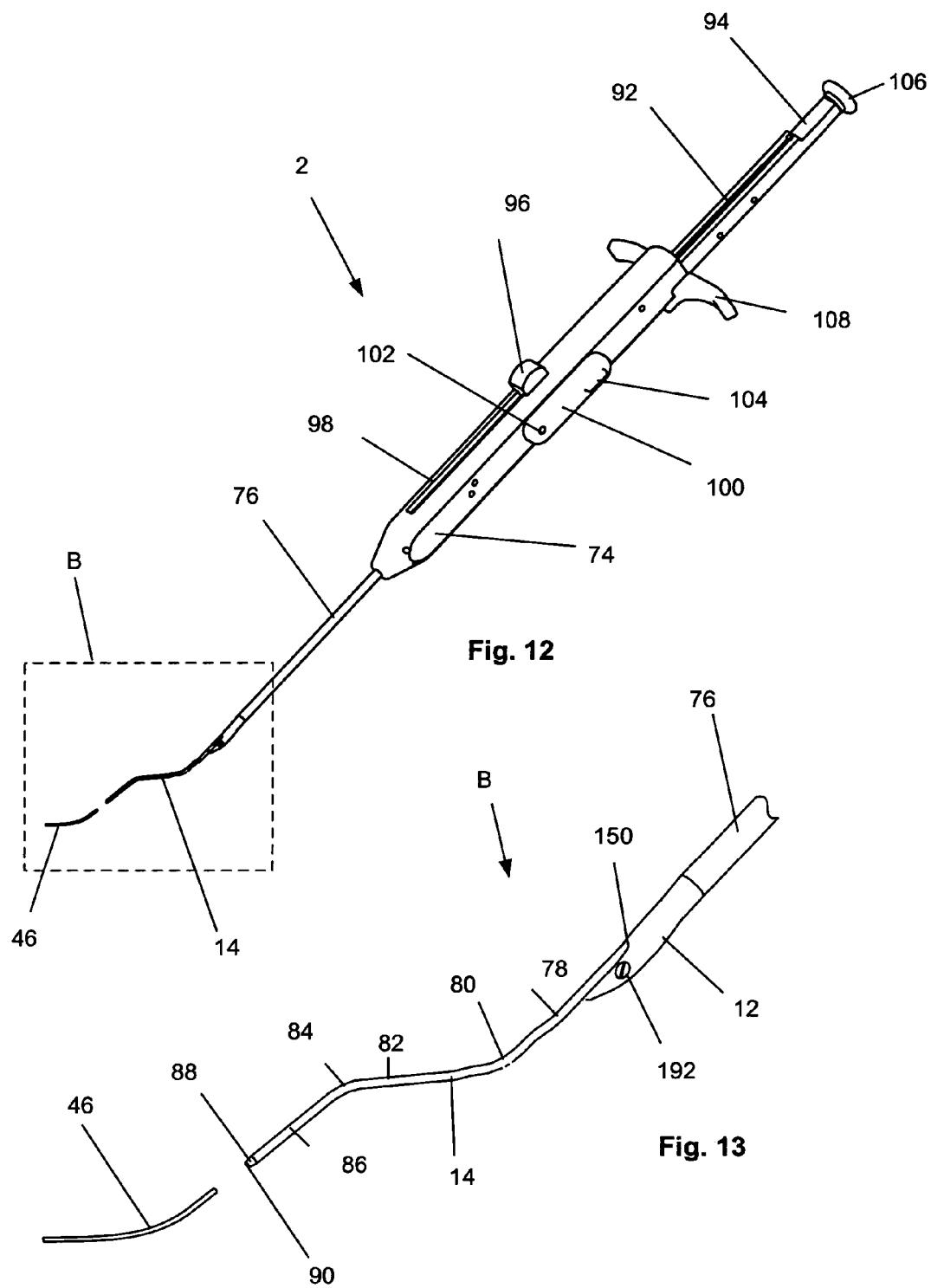

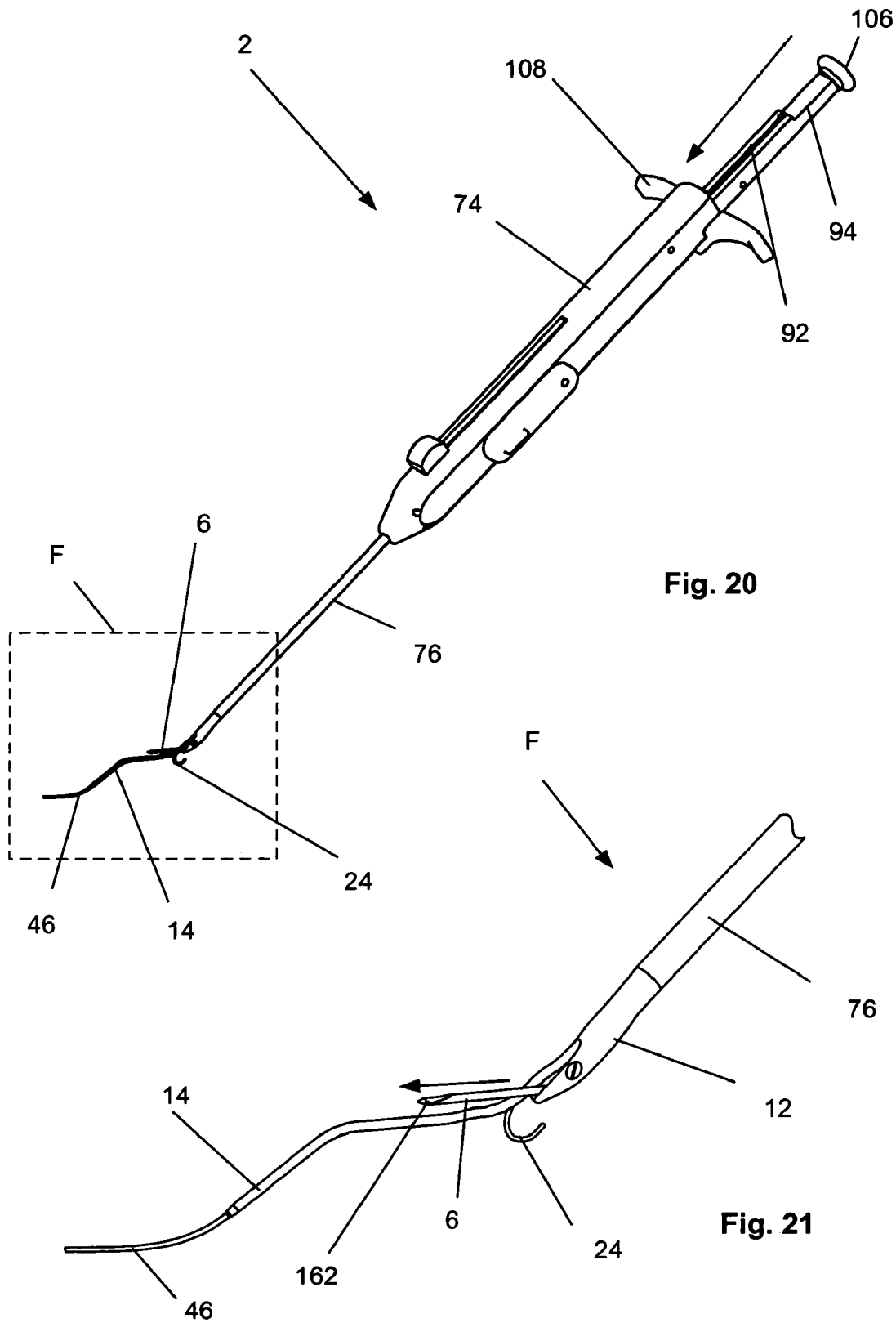

ACCESS AND CLOSURE DEVICE AND METHOD

CROSS-REFERENCE TO RELATED APPLICATION

This application claims the benefit under 35 U.S.C. §119(e) of U.S. Provisional Application 60/680,388 filed May 12, 2005, the content of which is incorporated herein by reference in its entirety.

BACKGROUND OF THE INVENTION

1. Field of the Invention

The present invention relates to the field of accessing a biological lumen and closing the access port thereby created.

2. Description of the Related Art

A number of diagnostic and interventional vascular procedures are now performed translumenally, where a catheter is introduced to the vascular system at a convenient access location—such as the femoral, brachial, or subclavian arteries—and guided through the vascular system to a target location to perform therapy or diagnosis. When vascular access is no longer required, the catheter and other vascular access devices must be removed from the vascular entrance and bleeding at the puncture site must be stopped.

One common approach for providing hemostasis is to apply external force near and upstream from the puncture site, typically by manual compression. This method is time-consuming, frequently requiring one-half hour or more of compression before hemostasis. This procedure is uncomfortable for the patient and frequently requires administering analgesics. Excessive pressure can also present the risk of total occlusion of the blood vessel, resulting in ischemia and/or thrombosis.

After hemostasis is achieved by manual compression, the patient is required to remain recumbent for six to eighteen hours under observation to assure continued hemostasis. During this time bleeding from the vascular access wound can restart, potentially resulting in major complications. These complications may require blood transfusion and/or surgical intervention.

Bioabsorbable fasteners have also been used to stop bleeding. Generally, these approaches rely on the placement of a thrombogenic and bioabsorbable material, such as collagen, at the superficial arterial wall over the puncture site. This method generally presents difficulty locating the interface of the overlying tissue and the adventitial surface of the blood vessel. Implanting the fastener too far from the desired location can result in failure to provide hemostasis. If, however, the fastener intrudes into the vascular lumen, thrombus can form on the fastener. Thrombus can embolize downstream and/or block normal blood flow at the thrombus site. Implanted fasteners can also cause infection and auto-immune reactions/rejections of the implant.

Suturing methods are also used to provide hemostasis after vascular access. The suture-applying device is introduced through the tissue tract with a distal end of the device located at the vascular puncture. Needles in the device draw suture through the blood vessel wall on opposite sides of the punctures, and the suture is secured directly over the adventitial surface of the blood vessel wall to close the vascular access wound.

To be successful, suturing methods need to be performed with a precise control. The needles need to be properly directed through the blood vessel wall so that the suture is well anchored in tissue to provide for tight closure. Suturing methods also require additional steps for the surgeon.

Due to the deficiencies of the above methods and devices, a need exists for a more reliable vascular closure method and device. There also exists a need for a vascular closure device and method that is self-sealing and secure. There also exists a need for a vascular closure device and method requiring no or few extra steps to close the vascular site.

BRIEF SUMMARY OF THE INVENTION

A method for accessing a biological lumen having a lumen wall and surrounding tissue is disclosed. The method includes forming a path between the lumen wall and the surrounding tissue. The method further includes extending the path through the lumen wall. The method also includes opening the path to the lumen.

The method of forming the path can include inserting a device between the lumen wall and the surrounding tissue. Extending the path can include inserting the device through the lumen wall. Opening the path can include inserting the device into the lumen. The method can include delivering a filler into the path.

The method can include filling the path. Filling the path can include delivering a filler into the path. The filler can have a solid-setting liquid. The filler can have an epoxy.

The method can include applying pressure to the path. Applying pressure to the path can include delivering filler adjacent to the path. Delivering filler adjacent to the path can include delivering filler between the lumen wall and the surrounding tissue. Delivering filler can include delivering filler in the lumen wall. Delivering filler can include delivering filler in the surrounding tissue.

Also disclosed is a method for forming an arteriotomy in a lumen having a lumen wall and surrounding tissue. The method includes translating a device substantially between the lumen wall and the surrounding tissue. The method further includes turning the device toward the lumen. The method also includes translating the device through the lumen wall. The method also includes removing the device from the lumen wall.

The surrounding tissue can have adventitia. Turning can include relaxation of a preformed configuration in the device.

The method can also include translating a guide through the device. Translating a guide can include translating the guide into the lumen. The method can also include translating a guide into the lumen. Translating a guide can include translating the guide through the device.

An access device for accessing a biological lumen is disclosed. The device has an introduction device having a relaxed configuration. The relaxed configuration has a first flat section, a first bend at an end of the first flat section, and a first slope extending at a first end from the first bend. The introduction device is configured to be translated with respect to the access device.

The relaxed configuration of the introduction device can have a second bend at a second end of the first slope, a second flat section extending at a first end from the second bend, a third bend at a second end of the second flat section, and a second slope extending from the third bend. The access device can have a delivery guide. The delivery guide can be configured to deliver the introduction device.

The access device can have an anchor. The anchor can extend from the delivery guide. The anchor can be configured to stabilize the access device with respect to the lumen.

A device for accessing a biological lumen is disclosed. The biological lumen has a lumen wall having a longitudinal lumen wall axis. The device has an elongated member that has a longitudinal member axis. The member is configured to access the lumen at a first angle.

BRIEF DESCRIPTION OF THE DRAWINGS

FIGS. 2 through 5 illustrate a method of using the arteriotomy device in a cross-section of a lumen.

FIG. 12 illustrates an embodiment of the arteriotomy device in a first configuration.

FIG. 13 is a close-up view of an embodiment of section B of FIG. 12.

FIG. 20 illustrates an embodiment of the arteriotomy device of FIG. 12 in a fourth configuration.

FIGS. 21 and 22 are close-up views of various embodiments of section F of FIG. 20.

DETAILED DESCRIPTION

Figure 1:
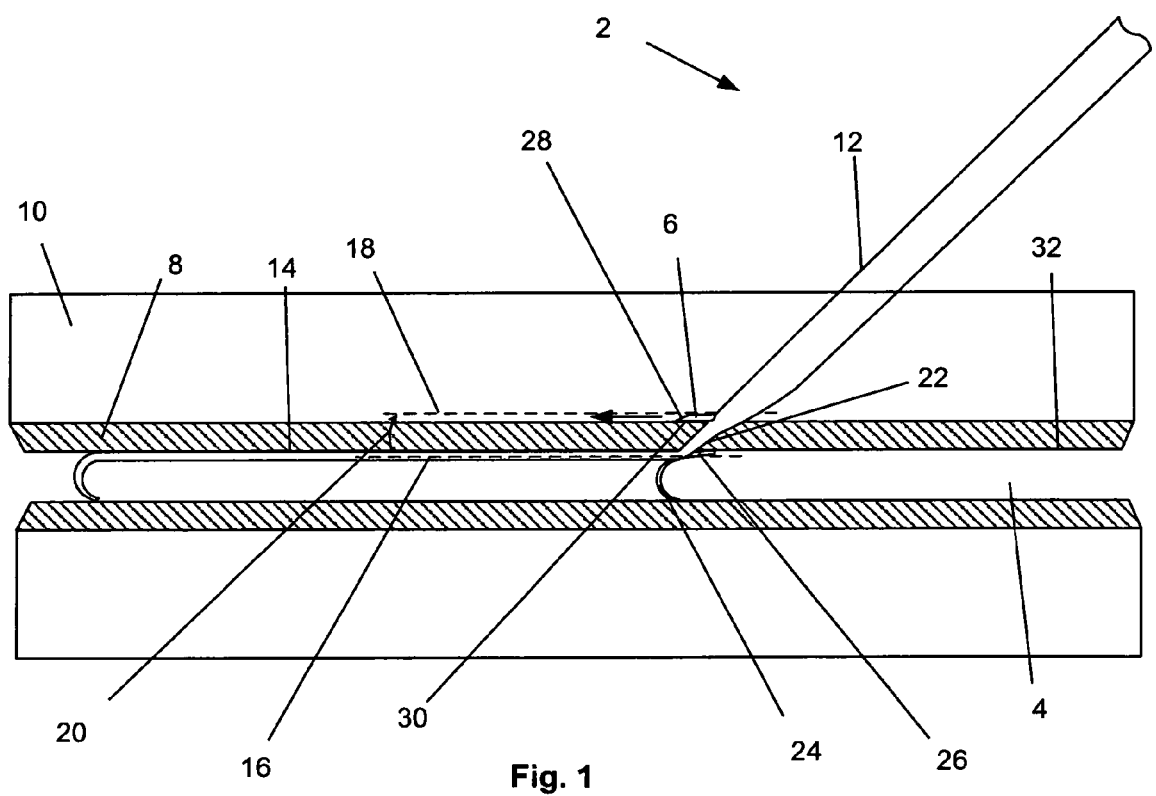
FIG. 1 is an embodiment of a method of using the arteriotomy device in a cross-section of a lumen.

U.S. patent application Ser. No. 10/844,247, filed 12 May 2004, is incorporated by reference herein in its entirety. Aspects, characteristics, components or complete embodiments of devices and methods disclosed therein can be used with anything disclosed herein.

FIGS. 1 through 6 illustrate embodiments of an arteriotomy device 2, and methods for accessing (e.g., percutaneously) a biological lumen 4 and deploying an introduction device 6 that can have one or more pre-formed bends. The biological lumen 4 can be surrounded by a lumen wall 8 (e.g., intima and/or media). The lumen wall 8 can be surrounded by surrounding tissue 10 (e.g., media and/or adventitia).

The arteriotomy device 2 can have a delivery guide 12. The delivery guide 12 can be slidably attached to an anchor 14. The anchor 14 can be rigid, flexible or combinations thereof. The anchor 14 can be resilient, deformable or combinations thereof. The anchor 14 can be retractable and extendable from the delivery guide 12. The anchor 14 can have a guide eye sheath or an attachable guidewire. The anchor 14 can have an integral, or multiple separate and fixedly attached, wound wire. The anchor 14 can have a wire coating, for example a lubricious coating and/or a coating made from urethane The anchor 14 can have an anchor longitudinal axis 16. The introduction device can have an introduction longitudinal axis 18. The intersection of the anchor longitudinal axis 16 and the introduction longitudinal axis 18 can be an introduction angle 20. The anchor 14 can be inserted into the biological lumen 4 using a Seldinger technique, modified Seldinger technique, or other method known to one having ordinary skill in the art.

The arteriotomy device 2 can be configured to deliver the introduction device at the introduction angle 20. The introduction device 6 can have an introduction longitudinal axis. The introduction angle 20 can be the intersection of the introduction longitudinal axis 18 and the anchor longitudinal axis 16. The introduction angle 20 can have an absolute value from about 0° to about 30°, more narrowly from about 0° to about 19°, yet more narrowly from about 0° to about 15°, yet more narrowly from about 5° to about 10°, for example about 10°.

Any or all elements of the arteriotomy device 2 or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CON-ICHROME® from Carpenter Metals Corp., Wyomissing, Pa.), molybdenum alloys (e.g., molybdenum TZM alloy, for example as disclosed in International Pub. No. WO 03/082363 A2, published Oct. 9, 2003, which is herein incorporated by reference in its entirety), tungsten-rhenium alloys, for example, as disclosed in International Pub. No. WO 03/082363, polymers such as polyester (e.g., DACRON® from E. I. Du Pont de Nemours and Company, Wilmington, Del.), carbon fiber composites (e.g., carbon fiber nylon composite, such as carbon fiber reinforced nylon 66), polypropylene, polytetrafluoroethylene (PTFE), expanded PTFE (ePTFE), polyether ether ketone (PEEK), nylon, polyetherblock co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polydioxanone, and pseudo-polyamino tyrosine-based acids, extruded collagen, silicone, zinc, echogenic, radioactive, radiopaque materials or combinations thereof. Examples of radiopaque materials are barium sulfate, zinc oxide, titanium, stainless steel, nickel-titanium alloys, tantalum and gold.

Any or all elements of the arteriotomy device 2, including supplemental closure devices, such as filler, or other devices or apparatuses described herein can be or have a matrix for cell ingrowth or used with a fabric, for example a covering (not shown) that acts as a matrix for cell ingrowth. The matrix and/or fabric can be, for example, polyester (e.g., DACRON® from E. I. du Pont de Nemours and Company, Wilmington, Del.), polypropylene, PTFE, ePTFE, nylon, extruded collagen, silicone or combinations thereof.

The elements of the arteriotomy device 2 and/or the filler and/or the fabric can be filled and/or coated with an agent delivery matrix known to one having ordinary skill in the art and/or a therapeutic and/or diagnostic agent. The agents within these matrices can include radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; niefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and *Chlamydia Pneumoniae*, *Brit. J Surgery* 88 (7), 935-940; Franklin et al, Uptake of Tetracycline by Aortic Aneurysm Wall and Its Effect on Inflammation and Proteolysis, *Brit. J Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Figure 45:
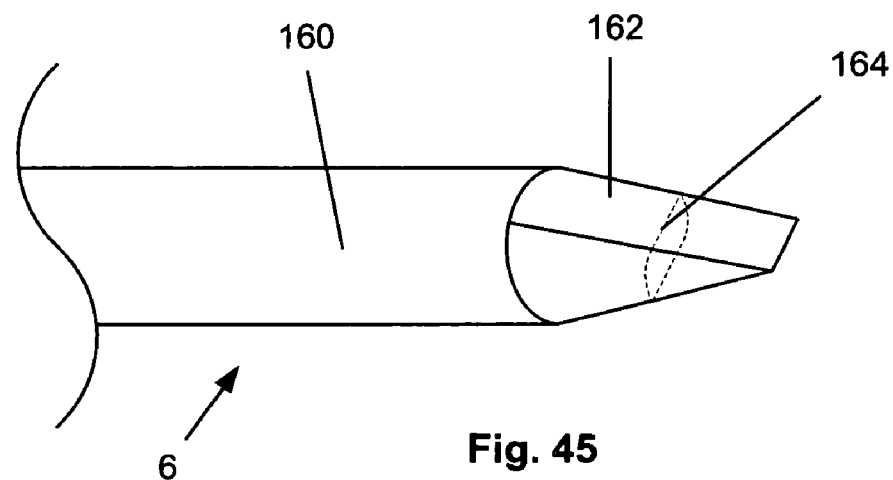
Figure 46:
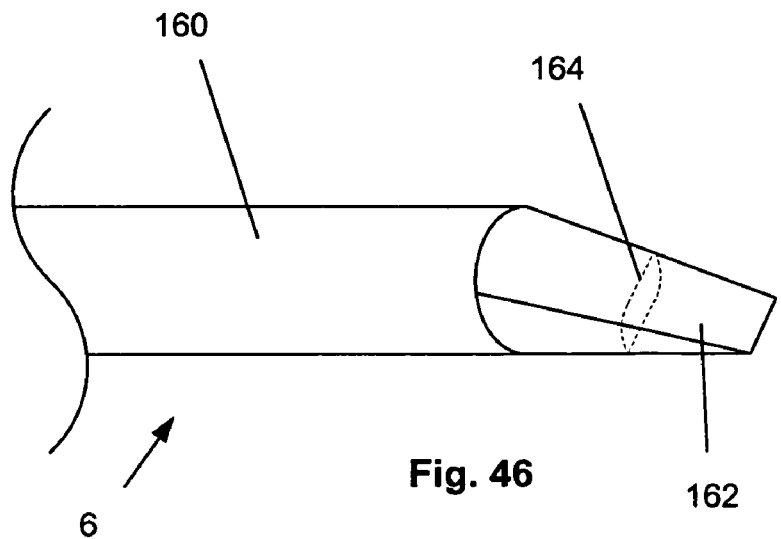

The delivery guide 12 can be deployed through the surrounding tissue 10 and into the lumen wall 8 and/or the lumen 4. As illustrated in FIGS. 45 and 46 of U.S. patent application Ser. No. 10/844,247 for a toggle deployment device, the arteriotomy device 2 can have a pressure check port. The pressure check port can be in fluid communication with a sensor or port on or near the handle of the arteriotomy device 2, such as an external lumen where blood flow can be observed, for example from flow from the end of an external tube or port and/or through a transparent or translucent window. The pressure check port can facilitate deployment of the arteriotomy device 2 to a location where the pressure check port is introduced to pressure, for example when the pressure check port enters the biological lumen 4. The sensor or port on or near the handle of the arteriotomy device 2 will signal that the pressure check port has been placed into the biological lumen 4 (e.g., by displaying a small amount of blood flow). The pressure check port can be deployed into the biological lumen 4 and then withdrawn from the biological lumen 4 to the point where the lumen wall 8 just stops the pressure in the pressure check port. An entry wall retainer port can additionally perform the function as described herein for the pressure check port.

The delivery guide 12 can form a first arteriotomy 22. When the anchor 14 is properly located in the lumen 4, a luminal retainer 24 and/or an entry wall retainer 26 can be deployed from the anchor 14 and/or the delivery guide 12. The anchor 14, and/or luminal retainer 24, and/or entry wall retainer 26 can be wires, rods, inflatable balloons, or combinations thereof. The anchor 14, and/or luminal retainer 24, and/or entry wall retainer 26 can be separate, integral or a single component.

Figure 2:
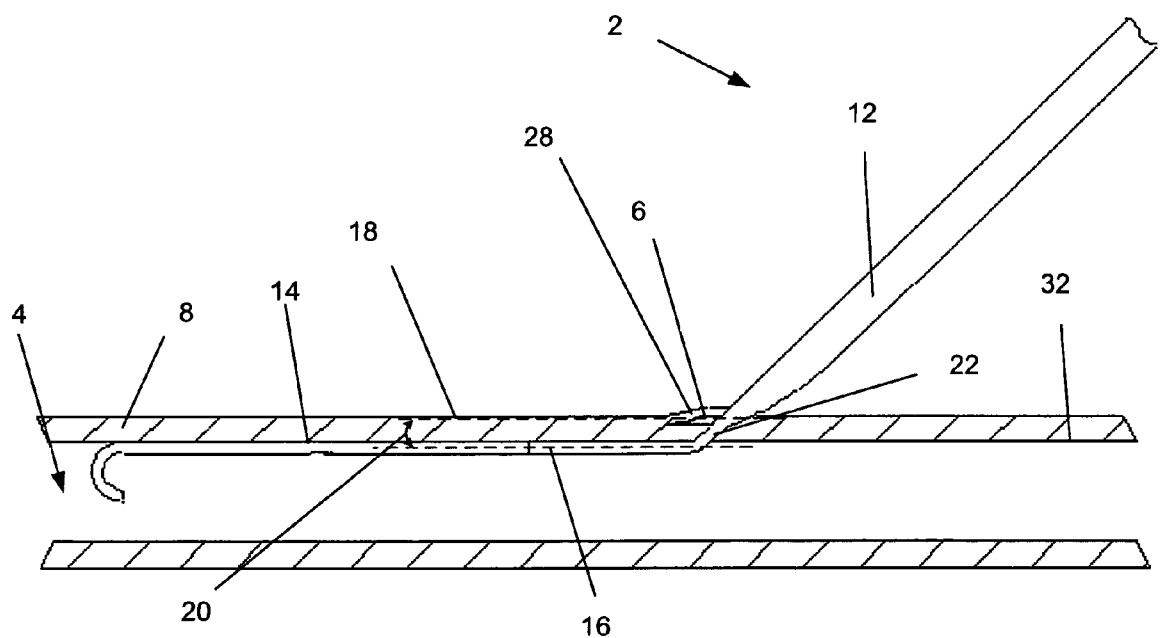

When the anchor 14 is properly located in the lumen 4, the introduction device 6 can be translated, as shown by arrow. The introduction device can form a second arteriotomy 28. The introduction device 6 can create a cleavage 30 between the lumen wall 8 and the surrounding tissue 10. The introduction device 6 can cleave a plane in the lumen wall 8, as shown in FIG. 2. The cleavage 30 and/or cleavage plane can be substantially parallel with a lumen wall surface 32. The introduction device 6 can be adjacent to the adventitia in a blood vessel. The introduction device 6 can be advanced along the subintimal or submedial cleavage plane in a blood vessel.

Once the lumen wall 8, and/or the surrounding tissue 10, and/or the cleavage 30 has been cleaved, a subintimal angioplasty can be performed as known to one having ordinary skill in the art. Once the lumen wall 8, and/or the surrounding tissue 10, and/or the cleavage 30 has been cleaved, a remote endarterectomy can be performed as known to one having ordinary skill in the art.

The introduction device 6 can have one or more straights and/or bends. Various bent introduction devices 34 and straight introduction devices 36 can be swapped during use to selectively cleave the lumen wall 8 and/or the surrounding tissue 10 and/or the cleavage 30. Tools, such as guides (e.g., guidewires), can be inserted through hollow introduction devices 6 to selectively cleave.

As shown in FIG. 3, when a bend 34 in the introduction device 6 moves into the lumen wall 8, the introduction device 6 can rotate and slope, as shown by arrow, toward the biological lumen 4. The bend 34 in the introduction device 6 can continue to rotate the introduction device 6 toward the biological lumen 4. When the introduction device 6 is sloping, the introduction angle 20 can be from about 0° to about 120°, more narrowly from about 5° to about 45°, yet more narrowly from about 10° to about 30°, for example about 15°.

FIG. 4 illustrates that the introduction device 6 can be further translated, as shown by arrow. The introduction device 6 can enter the lumen 4.

The introduction device 6 can pass through an introduction run 38 and an introduction rise 40. The introduction run 38 can be the component of the length of the introduction device 6 in the lumen wall 8 that is parallel to the lumen wall 8. The introduction run 38 can be the component of the length parallel to the lumen wall 8 between the opening of the second arteriotomy 28 on the outside of the lumen wall 8 and the opening of the second arteriotomy 28 on the inside lumen wall surface 32. The introduction run 38 can be from about 0.10 cm (0.010 in.) to about 3.810 cm (1.500 in.), for example about 0.64 cm (0.25 in.).

The introduction rise 40 can be the component of the length of the introduction device 6 in the lumen wall 8 that is perpendicular to the lumen wall 8. The introduction rise 40 can be the component of the length perpendicular to the lumen wall 8 between the opening of the second arteriotomy 28 on the outside of the lumen wall 8 and the opening of the second arteriotomy 28 on the inside lumen wall surface 32. The introduction rise 40 can be from about 0.51 mm (0.020 in.) to about 5.08 mm (0.200 in.), for example about 1.0 mm (0.040 in.).

An introduction slope can be the ratio of the introduction rise 40 to the introduction run 38. The introduction slope can be from about ½ to about ¹/₄₀ or less, for example about ⅙, also for example about ⅓. The introduction slope can be, for examples, equal to or less than about ½ or ⅓, more narrowly equal to or less than about ⅓ or ¼, yet more narrowly equal to or less than about ⅕ or ⅙, even still more narrowly than about equal to or less than about ¹/₁₀.

The introduction rise 40 and the introduction run 38 can be components of an introduction vector. The introduction run 38 can be the component of the introduction vector parallel to the lumen wall 8. The introduction rise 40 can be the component of the introduction vector perpendicular to the lumen wall 8. The introduction vector can be a vector from an outer opening 42 to an inner opening 44. The outer opening 42 can be a temporary or permanent opening in the lumen wall 8 or in the surrounding tissue 10 formed by the initial translation of the introduction device 6 out of the delivery guide 12. The inner opening 44 can be a temporary or permanent opening on the lumen wall surface 32.

Figure 5:
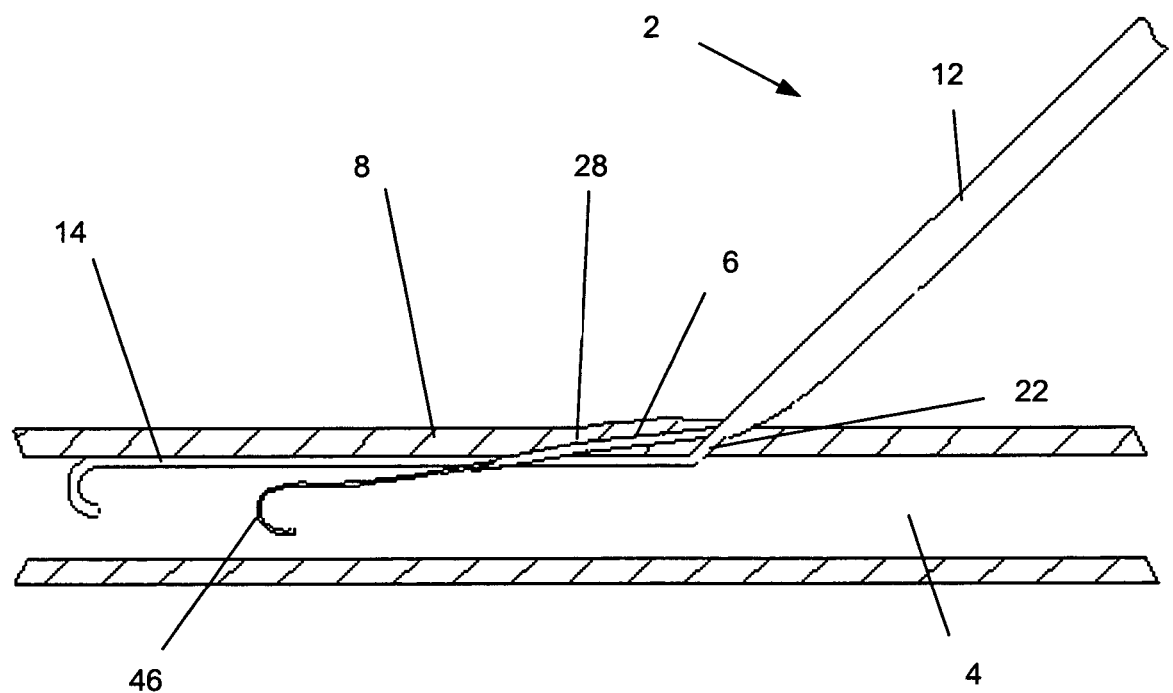

FIG. 5 illustrates that the introduction device 6 can act as a pathway for a luminal tool, for example a guidewire 46.

An introducer sheath (not shown) can be inserted over the guidewire 46 and/or over or through the introduction device 6. The introducer sheath can be less than about 22 French (7.3 mm, 0.29 in. diameter) or less than the diameter of the lumen to which the introducer sheath is introduced. The introducer sheath can be, for examples, about 6 French (2.3 mm, 0.092 in. diameter), and about 8 French (2.67 mm, 0.105 in. diameter). The introducer sheath can be known to one having ordinary skill in the art, for example the introducer sheath described in U.S. Pat. No. 5,183,464 to Dubrul, et al.

The introducer sheath can be inserted into the second arteriotomy 28. The introducer sheath can expand the second arteriotomy 28 to a desired or workable size. The introducer sheath can be inserted into the second arteriotomy 28 before and/or after and/or concurrently with when the filler, described infra, is deployed and/or other closure methods or devices are used.

Figure 6:
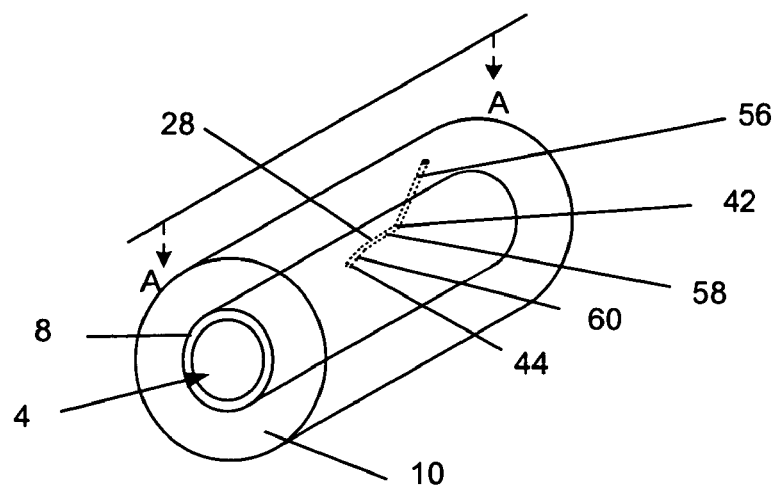
FIG. 6 illustrates a portion of an arteriotomized lumen.
Figure 7:
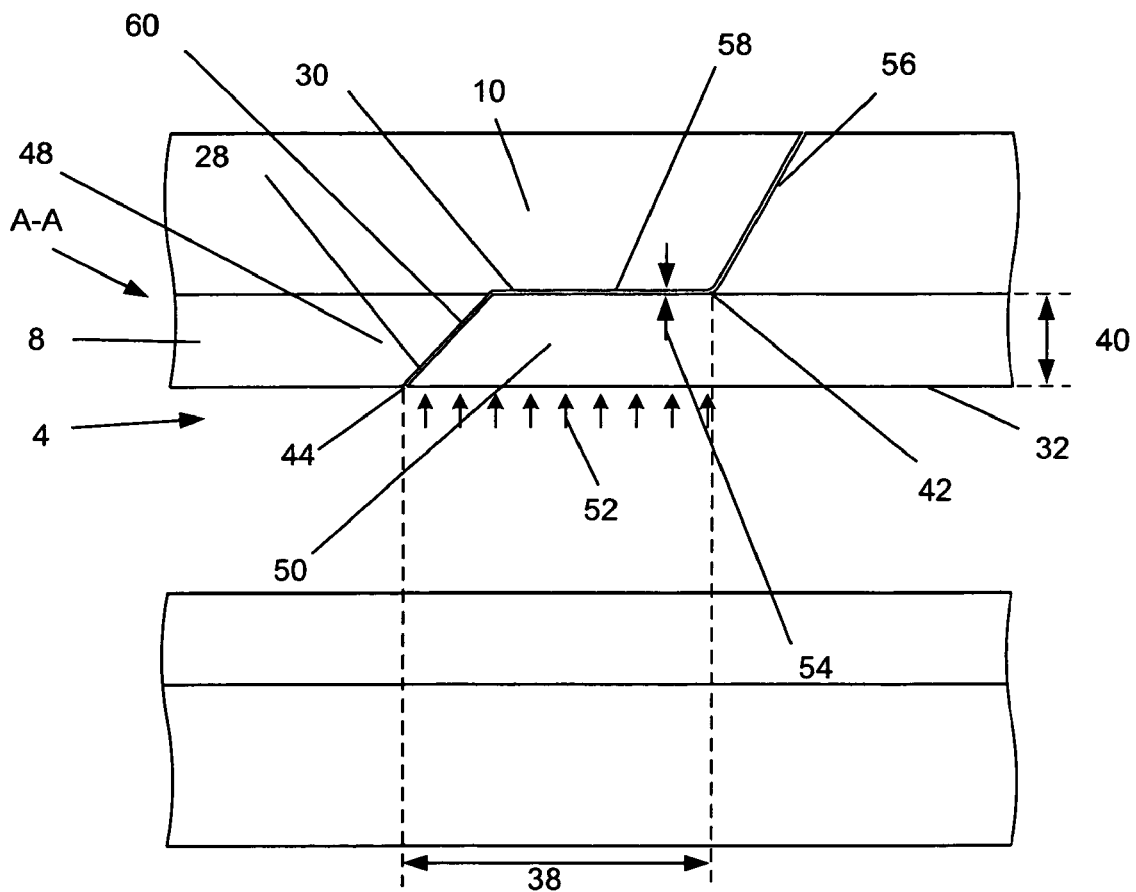
FIGS. 7 through 11 illustrate various embodiments of section A-A of FIG. 6.

FIGS. 6 and 7 illustrate an exemplary biological lumen 4 after the arteriotomy device 2 has been deployed to, and removed from, the biological lumen 4. The biological lumen 4 can have the second arteriotomy 28. The biological lumen 4 can have a first web 48 on one side of the second arteriotomy 28, and a second web 50 on the opposite side of the second arteriotomy 28. The blood pressure 52, shown by arrows, on the first and second webs 48 and 50 can self-seal the second arteriotomy 28.

The second arteriotomy 28 can have an arteriotomy cross-section that can have an arteriotomy diameter 54. The arteriotomy diameter 54 can be from about 0.5 mm (0.020 in.) to about 400 mm (15 in.), yet a narrower range from about 1.0 mm (0.040 in.) to about 10.2 mm (0.400 in.), for example about 2.54 mm (0.100 in.). The arteriotomy diameter 54 can be about the diameter of the introduction device 6.

The arteriotomy cross-section can be non-circular. The arteriotomy can have an arteriotomy width and an arteriotomy height. The arteriotomy width can be about half the circumference of the arteriotomy. The arteriotomy width can be from about 1.0 mm (0.040 in.) to about 10.2 mm (0.400 in.), for example about 4.06 mm (0.160 in.).

The arteriotomy height 152 can be less than about 0.51 mm (0.020 in.), more narrowly, less than about 0.38 mm (0.015 in.). The arteriotomy height can be from about 0.25 mm (0.010 in.) to about 1.3 mm (0.050 in.), for example about 0.38 mm (0.015 in.). The arteriotomy diameter, and/or height, and/or width can be small enough to enable cell growth, blood clotting, acoustic sealing, heat sealing, gluing, enhanced self-sealing and combinations thereof across the second arteriotomy 28.

The delivery guide 12 and/or other components of the arteriotomy device 2 can form a delivery path 56 during use. During percutaneous use, the delivery path can extend to the skin 138.

The second arteriotomy 28 can have a flat 58 and a slope 60. The flat 58 can be the cleavage 30 between the lumen wall 8 and the surrounding tissue.

Figure 8:
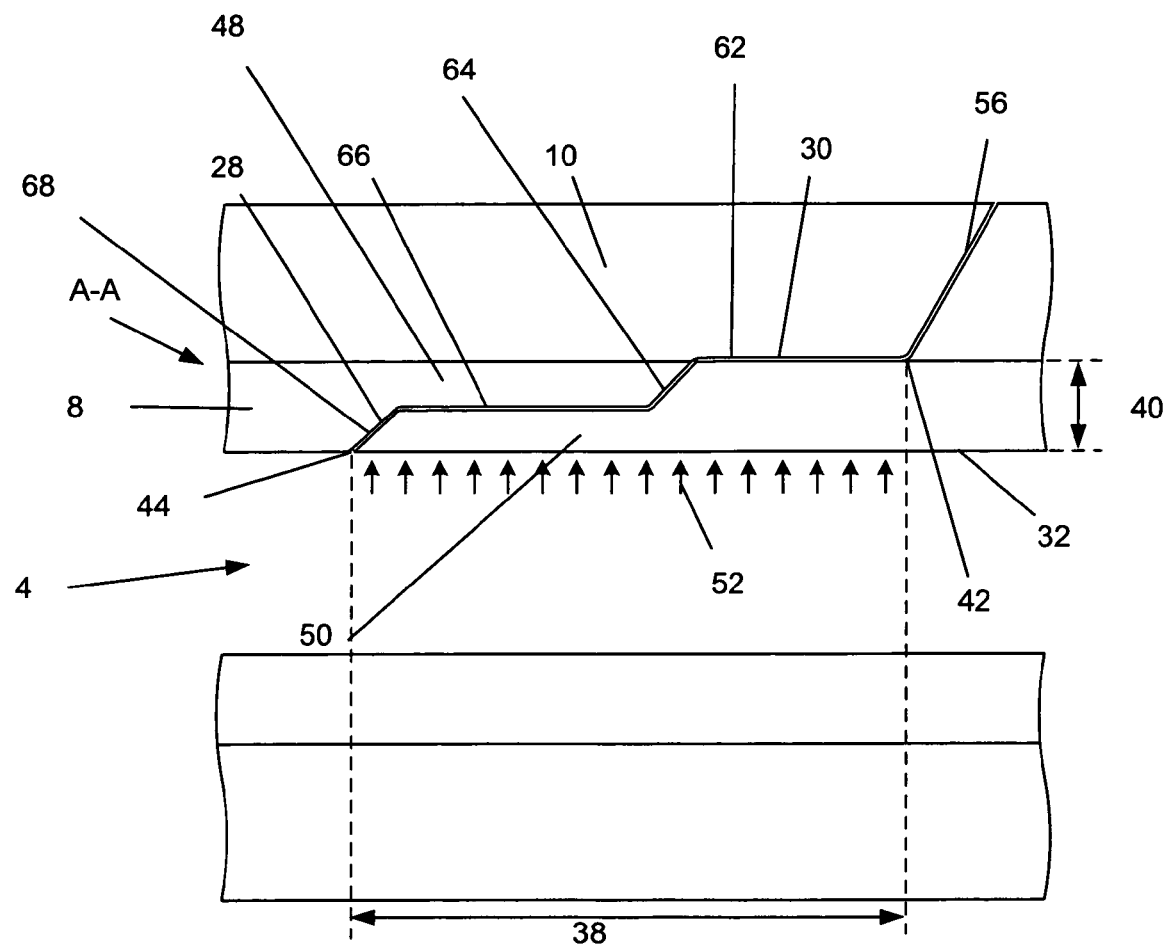

FIG. 8 illustrates that the second arteriotomy 28 can have a first flat 58, a first slope 64, a second flat 66, and a second slope 68. The second arteriotomy 28 having multiple flats and slopes can be made from one or more introduction devices 6 that can have various geometries.

Figure 9:
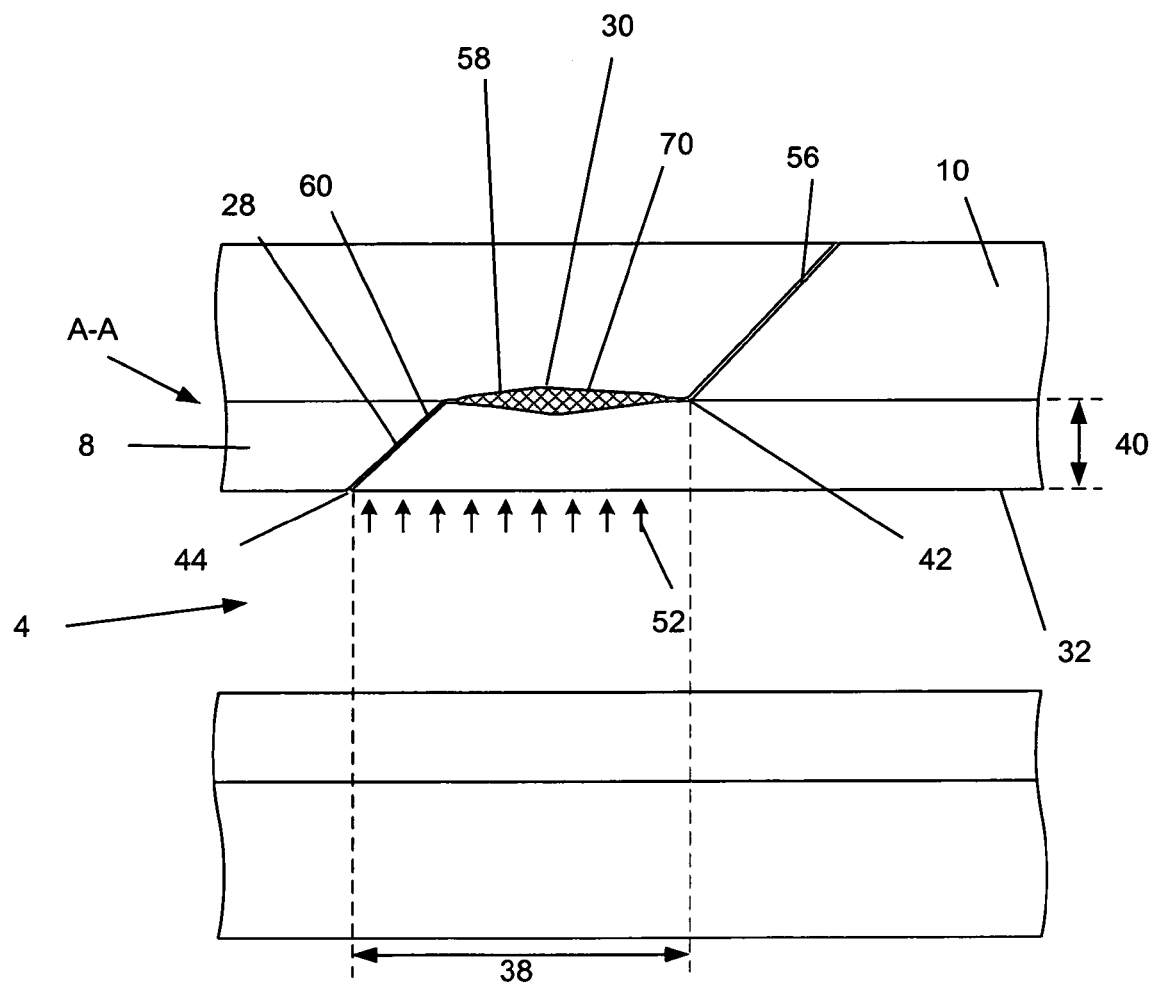

FIG. 9 illustrates that the second arteriotomy 28, for example in the flat 58 and/or the slope 60, can be filled with a filler 70. The filler 70 can be a solid single component, multiple solid components (e.g., beads), a biocompatible epoxy, or combinations thereof. The filler 70 can be completely or partially bioabsorbable, bioresorbable, bioadsorbable or combinations thereof. The filler 70 can be made from homografts, heterografts or combinations thereof. The filler 70 can be made from autografts, allografts or combinations thereof.

The filler 70 can be delivered (e.g., injected and/or implanted) into the second arteriotomy 28 through the surrounding tissue 10, for example by percutaneous injection. The filler 70 can be delivered (e.g., injected and/or implanted) into the second arteriotomy 28 through the second arteriotomy 28, for example via the introduction device 6 during introduction and/or removal of the introduction device 6.

The filler 70 can be permanently or temporarily deployed. The filler 70 can biodissolve after hemostasis is achieved and/or after the arteriotomy is substantially or completely healed. The filler 70 can be maintained from about 15 minutes to about 24 hours or more, for example about 120 minutes.

Figure 10:
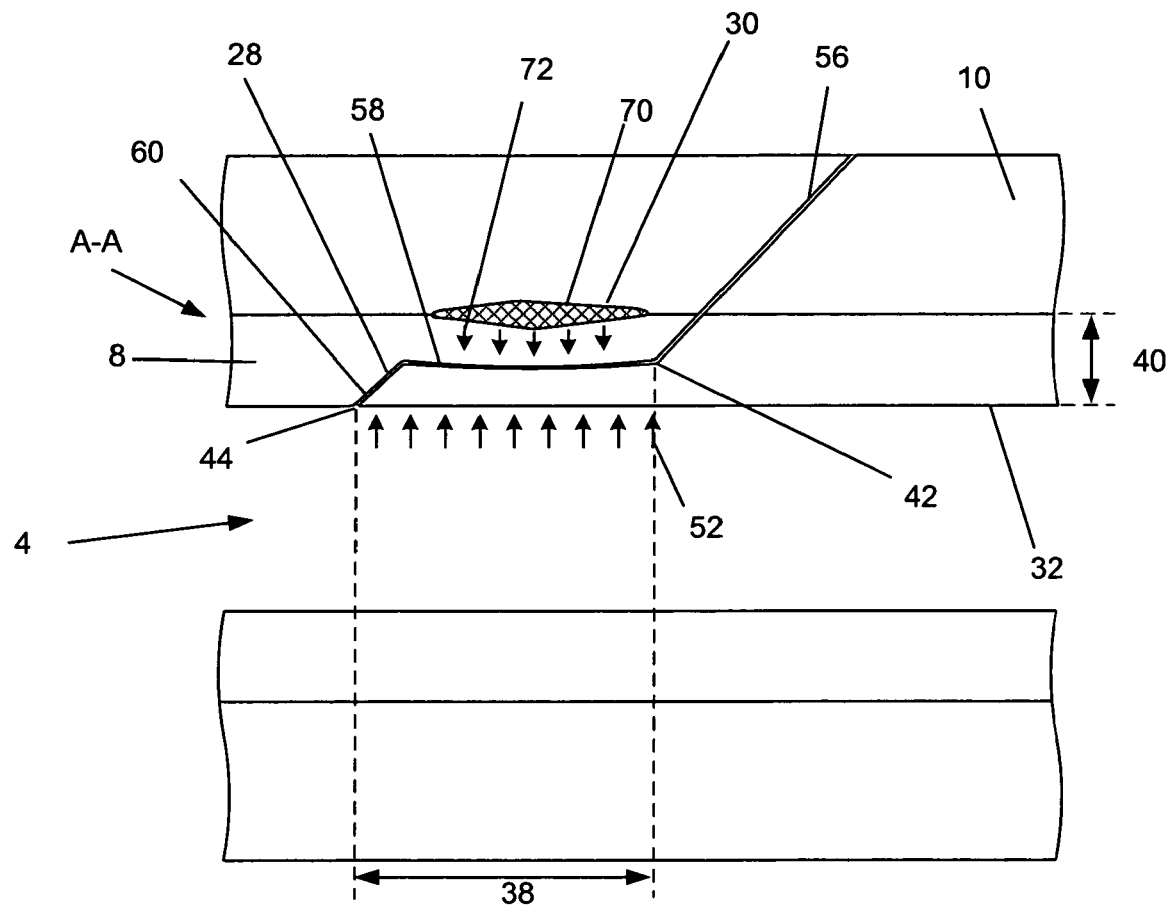

FIG. 10 illustrates that the filler can be in the cleavage 30, not in the second arteriotomy 28. The filler 70 can exert a filler pressure 72 on the second arteriotomy 28, for example on the flat 58 and/or slope 60. The second arteriotomy 28 can be compressed by the blood pressure 52 and the filler pressure 72.

Figure 11:
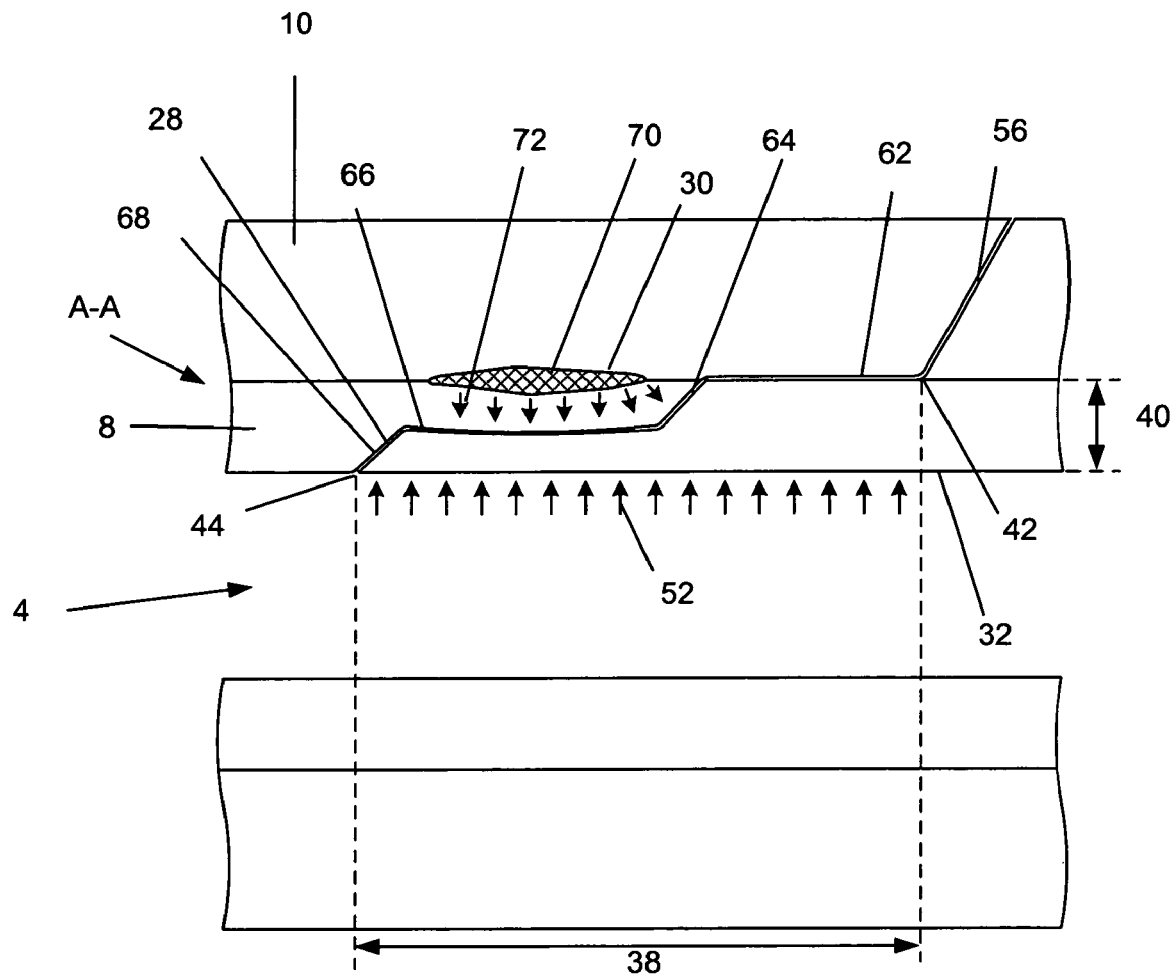

FIG. 11 illustrates that the filler can be in the in the cleavage 30, not in the second arteriotomy 28. The filler 70 can exert filler pressure 72 against the second flat 66 and/or first slope 64 and/or other sections of the second arteriotomy 28.

The filler 70 can be between the second arteriotomy 28 and the lumen 4 (not shown). The filler 70 can be in the surrounding tissue 10.

FIGS. 12 and 13 illustrate the arteriotomy device 2. The arteriotomy device 2 can have a handle 74 that can be integral with or fixedly attached to a delivery guide extension 76. The delivery guide extension 76 can be integral with or fixedly attached to the delivery guide 12. The anchor 14 can extend from, and be slidably and/or fixedly attached to or integral with, the delivery guide 12.

The anchor 14 can have an anchor first length 78 extending from the delivery guide 12. The anchor 14 can have an anchor first bend 80 at the end of the first anchor length 78 distal to the delivery guide 12. An anchor second length 82 can extend at a first end from the anchor first bend 80. A second end of the anchor second length 82 can have an anchor second bend 84. An anchor third length 86 can extend from the anchor second bend 84. The anchor third length 86 can terminate. The anchor 14 can have any combination of lengths and bends.

The radius of curvature for the anchor bends 80 and 84 can be from about 0.1 mm (0.004 in.) to about 2.0 mm (0.079 in.). The anchor lengths on both sides of any anchor bend can form an anchoring angle. The anchoring angles can be from about 90° to about 160°, more narrowly from about 120° to about 150°, for example about 135°. The anchor 14 can have a cross-section having an anchor diameter from about 0.38 mm (0.015 in.) to about 1.0 mm (0.039 in.), for example about 0.71 mm (0.028 in.).

The anchor third length 86 can have an anchor tip 88. The anchor tip 88 can be narrowed, widened, sharpened, dulled, or otherwise configured to promote sharp or blunt dissection. The anchor tip 88 can have an anchor end port 90. The anchor end port 90 can be in communication with an anchor guidewire lumen (not shown). The anchor guidewire lumen can be in communication with a guide lumen 92 in the delivery guide extension 76, and/or the handle 74, and/or a third control 94. The guide lumen 92 can have open access along the delivery guide extension 76, and/or along the handle 74, and/or along the third control 94 (as shown).

The handle 74 can have a first control 96. The first control 96 can be slidably attached to a control slide 98. The first control 96 can be configured to be ergonomically receptive to be activated a digit and/or a palm.

The handle 74 can have a second control 100. The second control 100 can be rotatably attached to the handle 74, for example at a control pivot 102. The second control 100 can have a tab 104. The tab 104 can be configured to be ergonomically receptive to be activated by a digit and/or a palm.

The handle 74 can have a third control 94. The third control can be slidably attached to the handle 74. The third control 94 can have or be a plunger. The third control 94 can have a press 106. The press 106 can be configured to be ergonomically receptive to be activated by a digit and/or a palm. The handle 74 can have one or more grips 108. The grips 108 can be configured to be ergonomically receptive to be held by a digit and/or a palm.

The configuration of any of the first, second or third controls 96, 100 and 94 can be any configuration (e.g., the first control can have the rotatable lever of the second control 100).

A guidewire 46 can be in proximity to the anchor tip 88.

Figure 14:
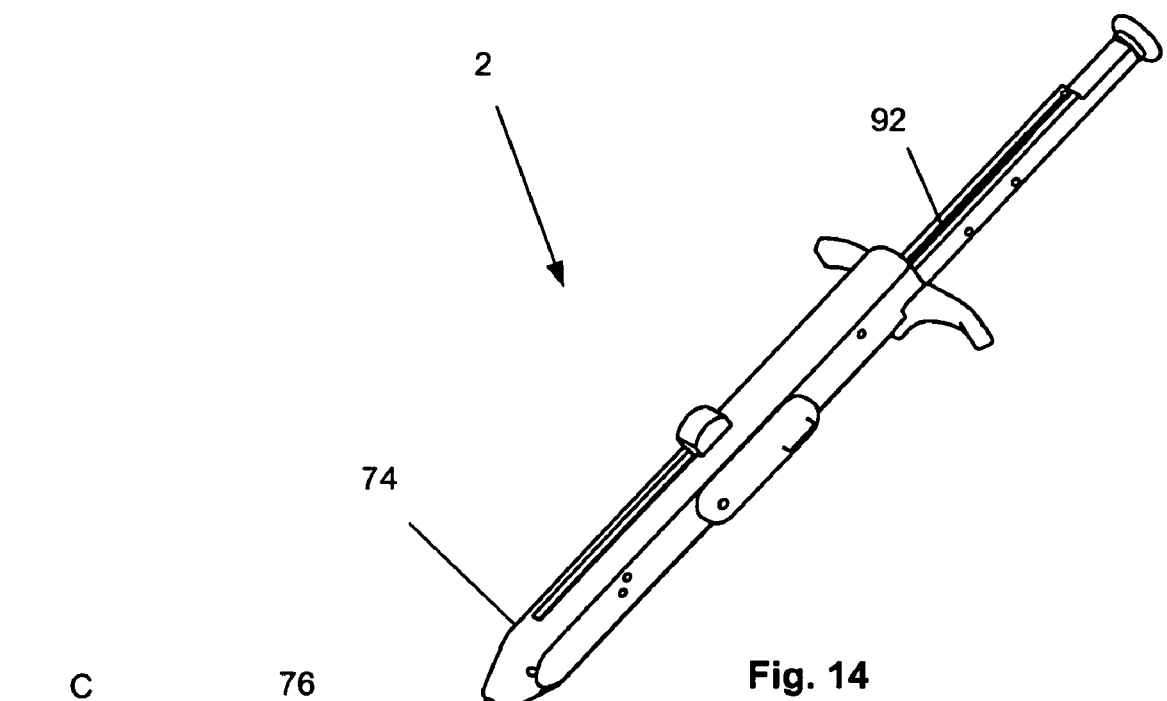
FIG. 14 illustrates an embodiment of the arteriotomy device of FIG. 12 in a second configuration.
Figure 15:
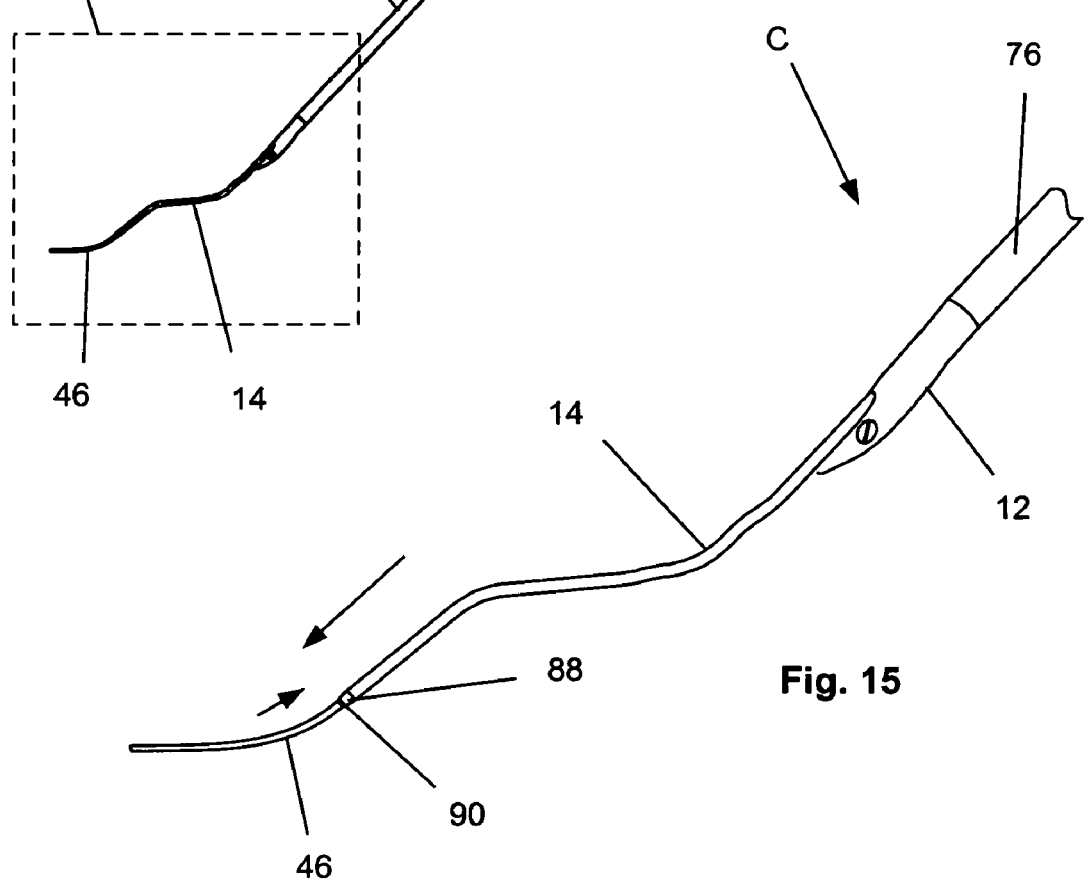
FIG. 15 is a close-up view of an embodiment of section C of FIG. 14.

FIGS. 14 and 15 illustrate that the guidewire 46 can be inserted into the anchor end port 90, as shown by arrows. The guidewire 46 can be fed through the anchor guidewire lumen and the guide lumen 92. The guidewire 46 can exit through the open section of the guide lumen 92.

The guidewire 46 can be used to deploy the arteriotomy device to a desired location in a lumen. The arteriotomy device 2 can be translated, for example percutaneously, over and along the guidewire 46. If the guidewire 46 is in a lumen, the arteriotomy device 2 can be translated along the guidewire 46, for example, until blood appears at the pressure check port.

Figure 16:
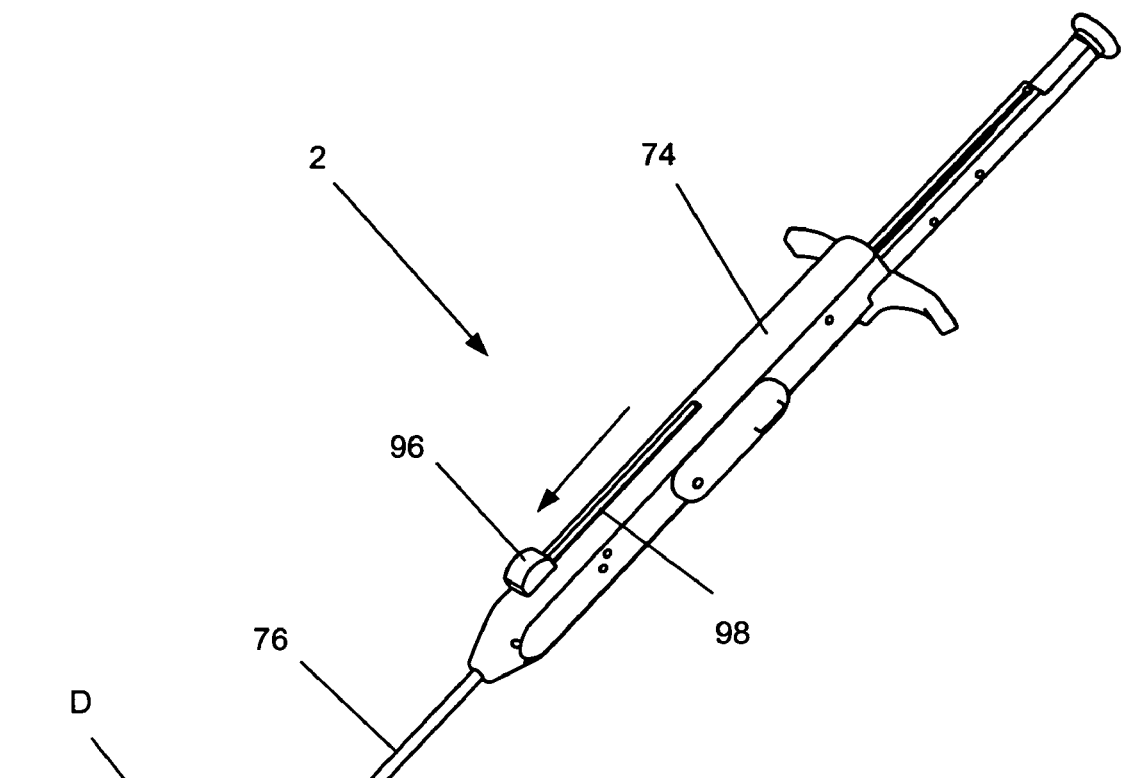
FIG. 16 illustrates an embodiment of the arteriotomy device of FIG. 12 in a third configuration.

FIG. 16 illustrates that the first control 96 can be activated, as shown by arrow. The first control 96 can be translated along the control slide 98. Activating the first control 96 can translatably and/or rotatably deploy the luminal retainer 24, as shown by arrow in FIG. 17.

The luminal retainer 24 can be a wire, scaffold or stent—for example made from a deformable or resilient material, such as a shape memory alloy—an inflatable balloon, or combinations thereof. Intralumenal inflatable balloons, such as those inflated with saline solution or carbon dioxide, are known to those having ordinary skill in the art. The luminal retainer 24 can extend into the delivery guide 12.

Figure 17:
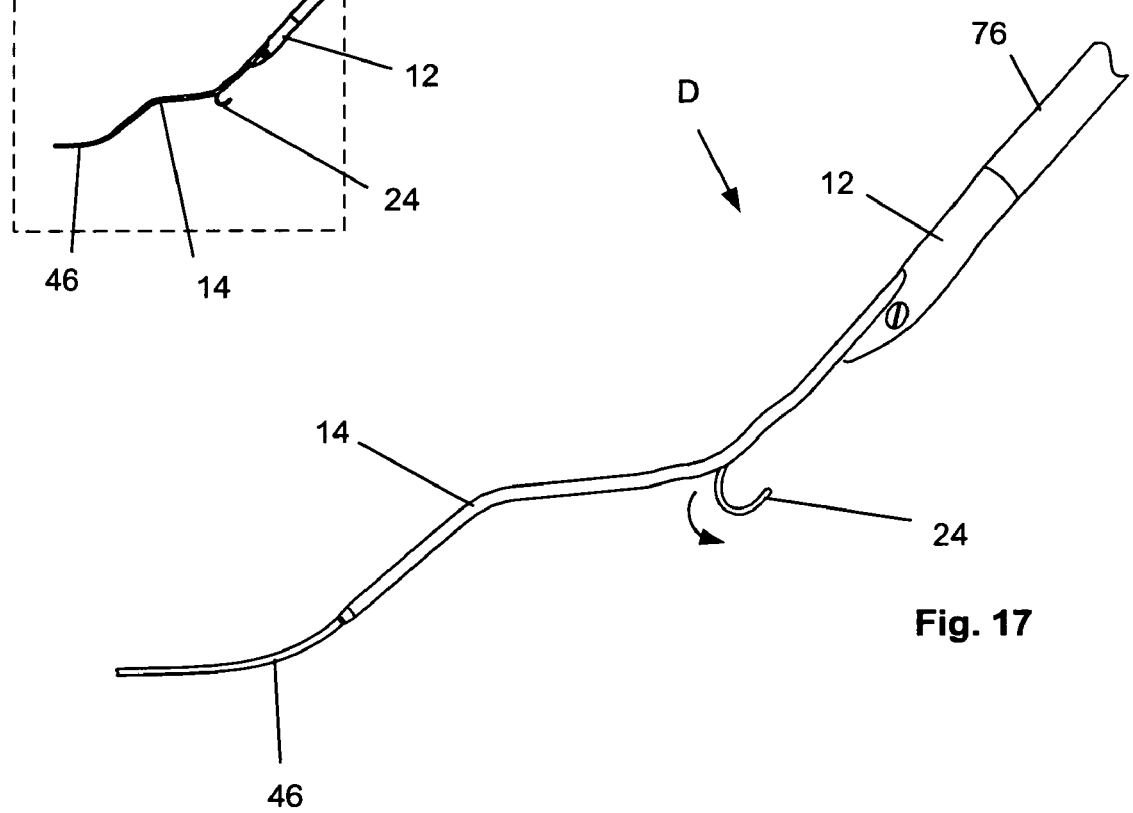
FIG. 17 is a close-up view of an embodiment of section D of FIG. 16.

FIG. 17 illustrates that the luminal retainer 24 can be deployed, as shown by arrow, for example due to the activation of the first control 96. The luminal retainer 24 can have a first stressed configuration. The luminal retainer 24 can have a second relaxed configuration. The luminal retainer 24 can be in a relaxed of a stressed configuration prior to deployment. The luminal retainer 24 can be in a relaxed or a stressed configuration after deployment. The relaxed configuration of the luminal retainer 24 can be the deployed configuration of the luminal retainer 24.

The luminal retainer 24 can be configured to press against the lumen 4 during use. The luminal retainer can be deployed by translating, rotating or a combination thereof, with respect to the anchor 14.

The luminal retainer 24 can deploy from the anchor 14. The luminal retainer 24 can deploy from a luminal retainer port (not shown). The luminal retainer 24 can have a luminal retainer deployed diameter. The luminal retainer deployed diameter can be from about 2.54 mm (0.100 in.) to about 10.2 mm (0.400 in.), for example about 6.35 mm (0.250 in.).

Figure 18:
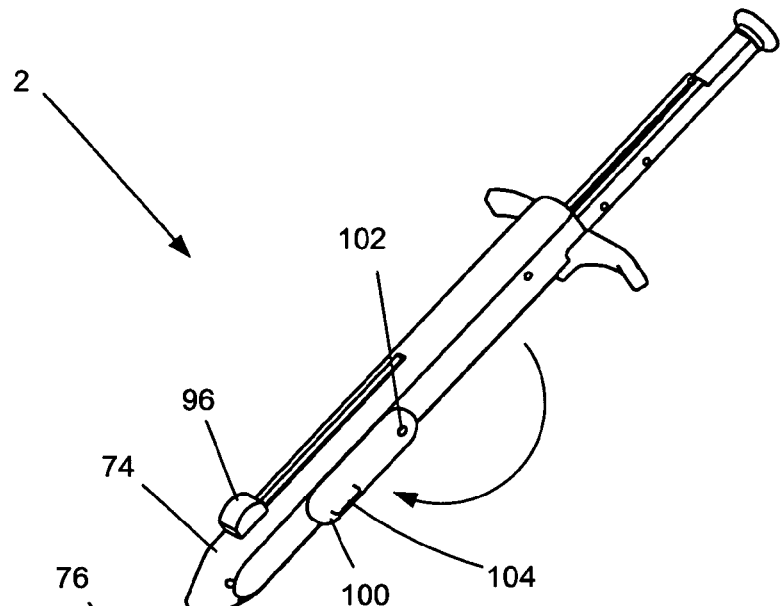
FIG. 18 illustrates an embodiment of the arteriotomy device of FIG. 12 in a fourth configuration.

FIG. 18 illustrates that the second control 100 can be activated, as shown by arrow. The second control 100 can be rotated around the control pivot 102. Activating the second control can translatably and/or rotatably retract the anchor 14, as shown by arrows in FIG. 19.

Figure 19:
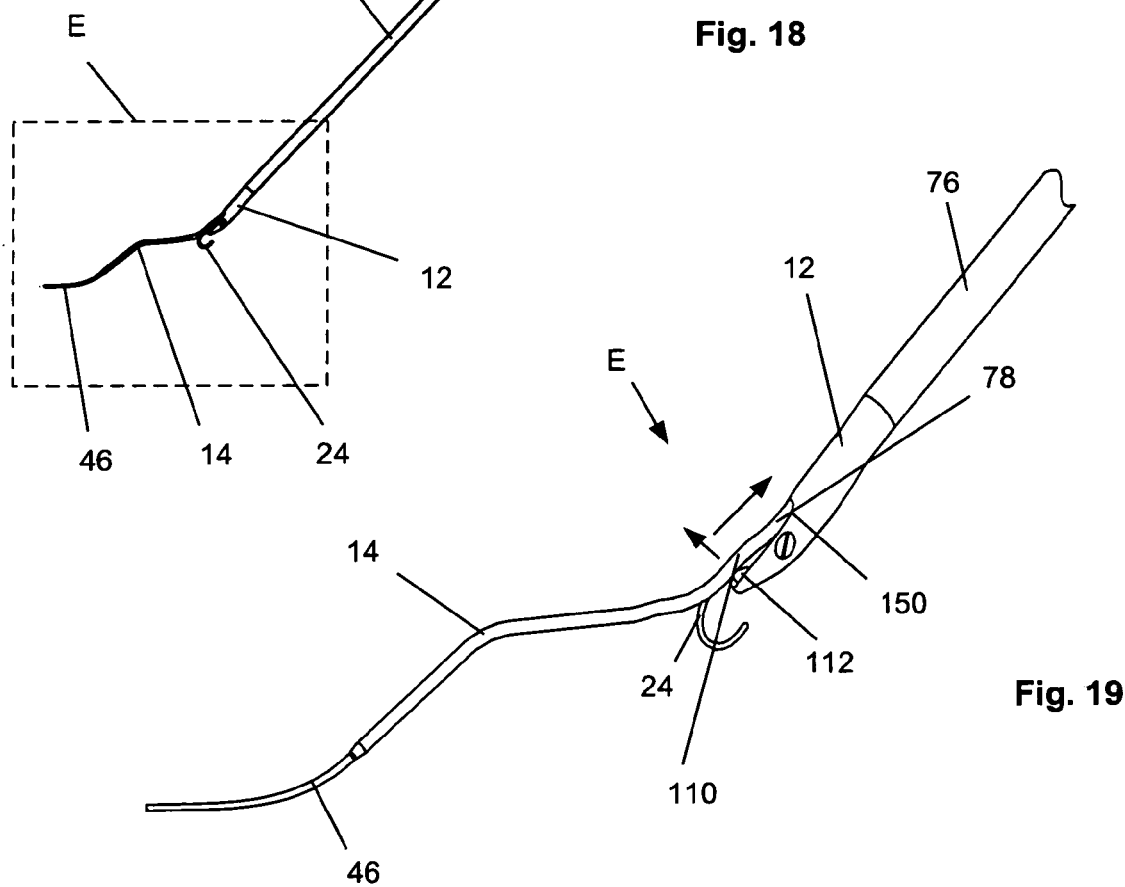
FIG. 19 is a close-up view of an embodiment of section E of FIG. 18.

FIG. 19 illustrates that the anchor 14 can translate both parallel and/or perpendicular to the delivery guide 12.

The anchor first length 78 can have an anchor shift 110 or small inflection. The anchor shift 110 can be configured wherein the anchor first length 78 shifts perpendicular to the longitudinal axis of the delivery guide 12, as seen in FIG. 19. An introduction lumen exit port 112 can be covered by the anchor first length 78, for example, before the anchor is retracted into the delivery guide 12.

When the anchor is retracted into the delivery guide 12, an introduction lumen exit port 112 can be exposed. When the anchor is retracted into the delivery guide 12, the anchor shift 110, laterally positioned compared to the rest of the anchor first length 78, can expose the introduction lumen exit port 112. When the anchor is retracted into the delivery guide 12, the anchor shift 110, laterally positioned compared to the rest of the anchor first length 78, can force the entire anchor 14 to move laterally, thereby exposing the introduction lumen exit port 112.

FIG. 20 illustrates that the third control 94 can be activated, as shown by arrow. The third control 94 can be translated with respect to the handle 74. Activating the third control can translatably deploy the introduction device 6, as shown by arrow in FIG. 21.

The introduction device 6 can have an introduction device diameter. The introduction device diameter can be from about 0.25 mm (0.010 in.) to about 1.0 mm (0.039 in.), for example about 0.56 mm (0.022 in.).

The arteriotomy device 2 can be configured to deploy the introduction device 6 from the anchor 14 and/or the delivery guide 12 (as shown). The anchor 14 and/or delivery guide 12 can have the introduction lumen exit port 112. The introduction device 6 can deploy through the introduction lumen exit port 112. The introduction device 6 can be a solid or hollow needle, or combinations thereof.

Figure 22:
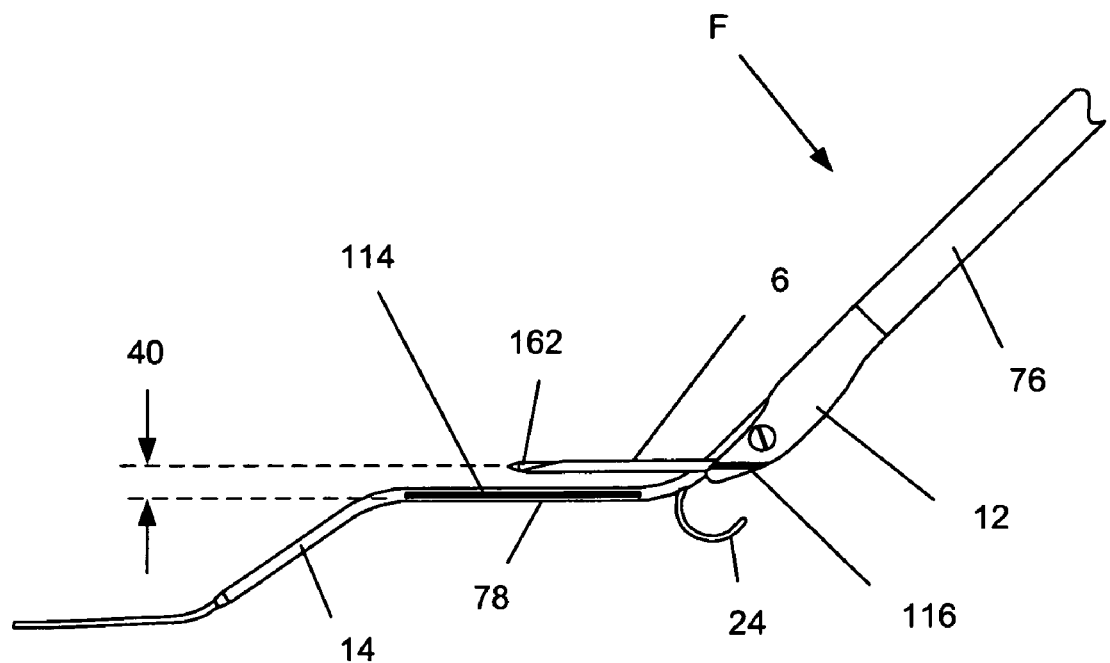

FIG. 22 illustrates that the distance perpendicular to the introduction device 6 between the introduction lumen exit port 112 to the anchor first length 78 can be substantially and/or completely equal to the introduction rise 40. The anchor 14 can have one or more radiopaque marks. For example, the anchor first length 78 can have a first radiopaque mark 114. The first radiopaque mark 114 can be significantly longer along the anchor first length 78 than the first radiopaque mark 114 is tall or wide. The delivery guide 12 can have a second radiopaque mark 116. The second radiopaque mark 116 can be parallel and aligned with the path of the introduction device 6 where the introduction device 6 exits the introduction lumen exit port 112. The user can view a radiograph or to assist in the placement of the arteriotomy device 2.

Figure 23:
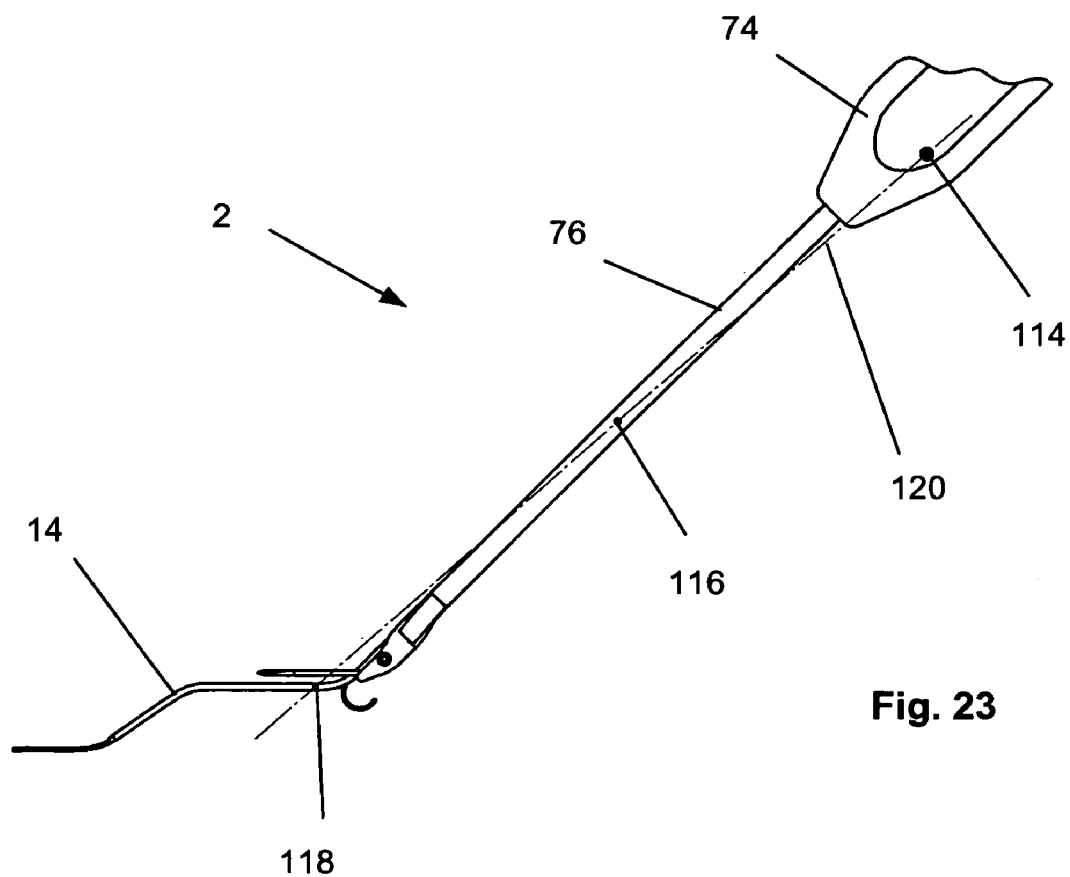
FIG. 23 illustrates an embodiment of the arteriotomy device.

FIG. 23 illustrates that the arteriotomy device can have a first, second and third radiopaque marks 114, 116 and 118. The first radiopaque mark 114 can be on the handle. The second radiopaque mark 116 can be on the delivery guide extension 76. The third radiopaque mark 118 can be on the anchor 14. A straight alignment axis 120 can pass through the first, second and third radiopaque marks 114, 116 and 118. The user can utilize the alignment axis 120 to assist in the placement of the arteriotomy device 2, for example while viewing a radiograph.

The radiopaque marks can be marks for any type of medical imagining. For example, the marks could be sono-opaque and/or sono-reflective for use with sonographs.

Figure 24:
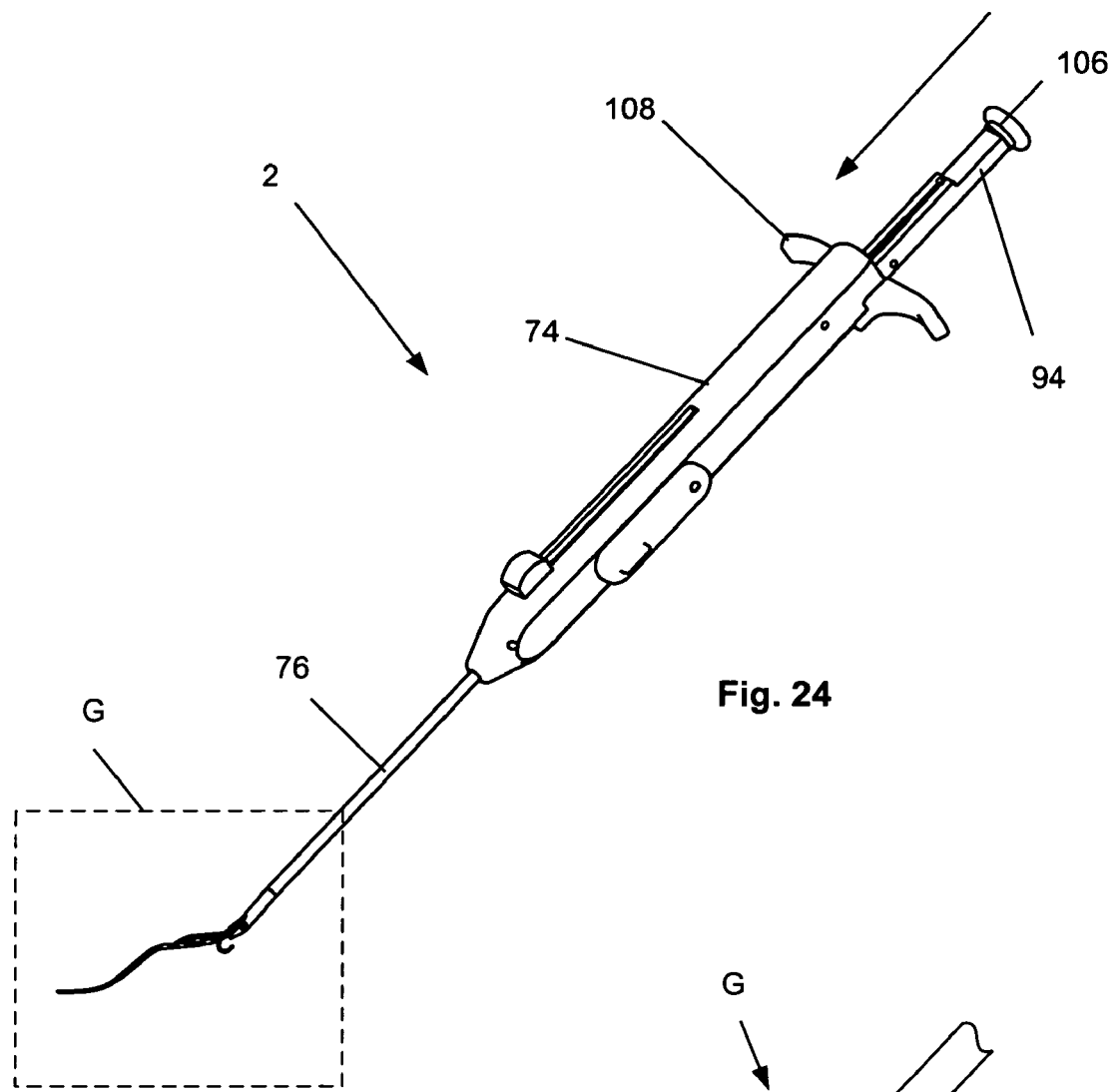
FIG. 24 illustrates an embodiment of the arteriotomy device of FIG. 12 in a fifth configuration.
Figure 25:
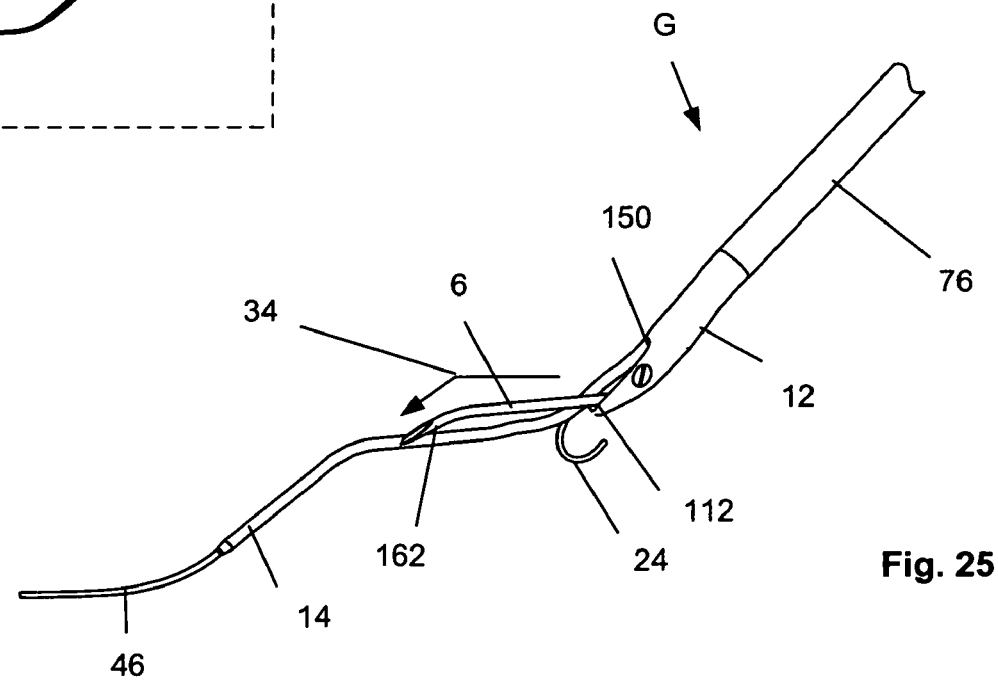
FIG. 25 is a close-up view of an embodiment of section G of FIG. 24.

FIG. 24 illustrates that the third control 94 can be activated further, for example, by continuing to translate the third control 94 toward the handle 74, as shown by arrow. Activating or re-activating the third control can translatably deploy the introduction device 6, as shown by arrow in FIG. 25.

The introduction device 6 can have a bend 34. The bend 34 can be in a relaxed configuration of the introduction device 6. If the introduction device 6 is deployed far enough, the bend 34 can rotate the introduction device 6 toward the lumen 4.

The first, second and third controls 96, 100 and 94 can have lockouts to prevent the controls 96, 100 and 94 from being activated incorrectly (e.g., to prevent use in the wrong order).

Figure 26:
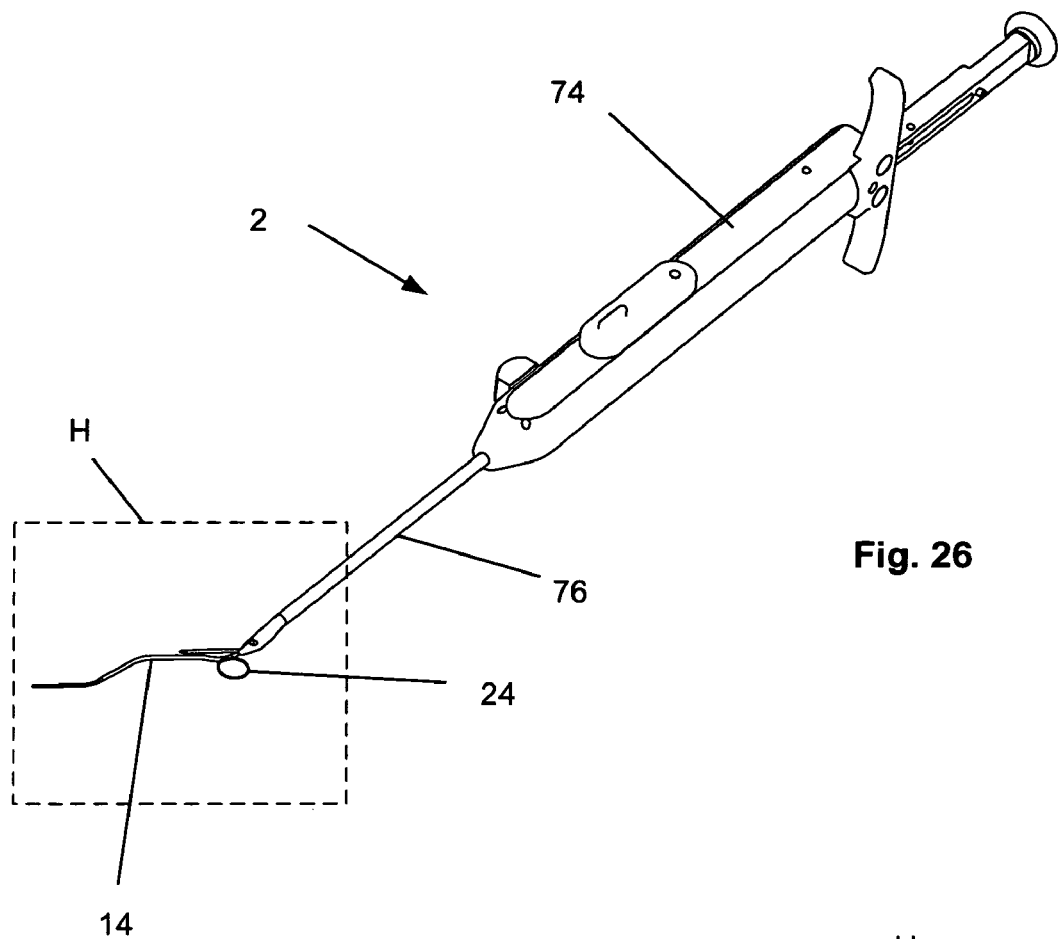
FIG. 26 illustrates an embodiment of the arteriotomy device.
Figure 27:
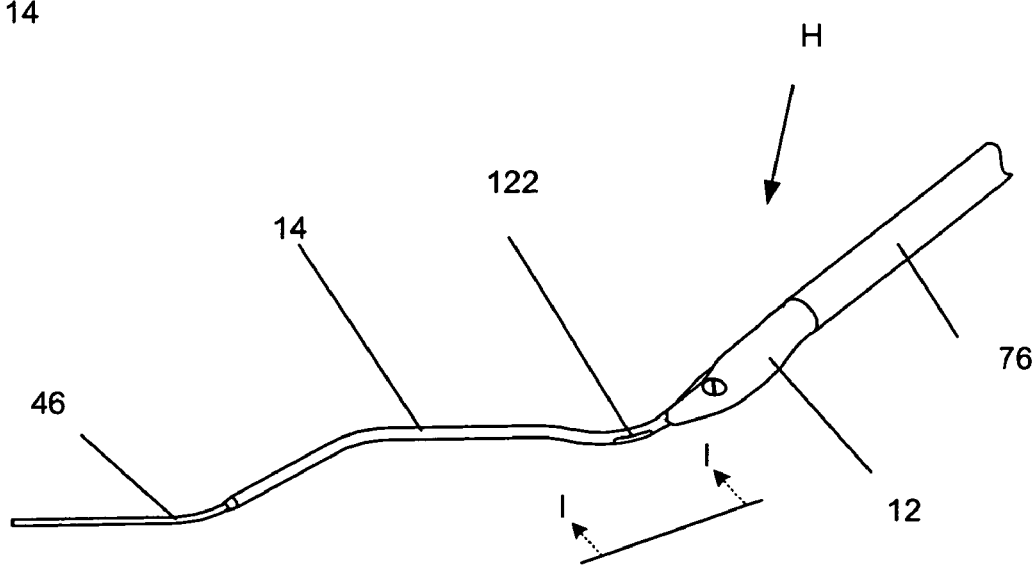
FIG. 27 is a close-up view of an embodiment of section H of FIG. 26.

FIG. 26 illustrates that the luminal retainer 24 can form a circular, oval, or spiral configuration. FIG. 27 illustrates that the anchor 14 can have a luminal retainer exit port 122.

Figure 28:
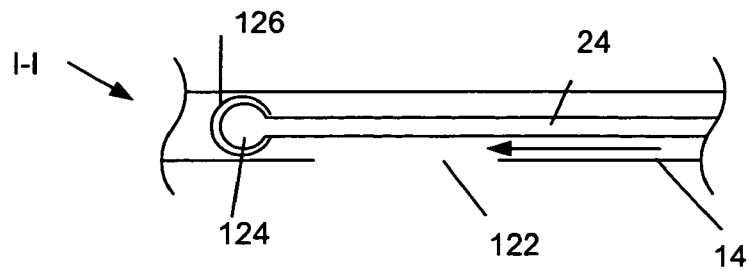
FIGS. 28 through 32 illustrate various embodiments of cross-section I-I of FIG. 27.

FIGS. 28 through 32 illustrate various configurations of the luminal retainer 24 in the anchor 14 prior to deployment. FIG. 28 illustrates that one end of the luminal retainer can be fixedly or rotatably attached to the anchor 14. The luminal retainer 24 can have a ball 124 and the anchor 14 can have a socket 126. The ball 124 can have an interference fit in the socket 126. When the deployment force is applied, shown by arrow, the luminal retainer 24 can relax, if pre-stressed (e.g., heat-treated to a specific shape), and/or be forced into buckling out through the luminal retainer exit port 122.

Figure 29:
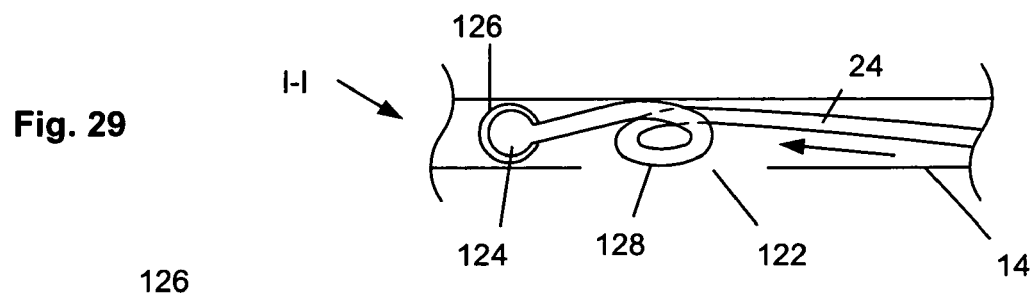

FIG. 29 illustrates that the luminal retainer 24 can be loaded in a loop or spiral configuration in the anchor 14. When the deployment force is applied, as shown by arrow, the loop 128 will naturally expand and exit the luminal retainer port 122.

Figure 30:
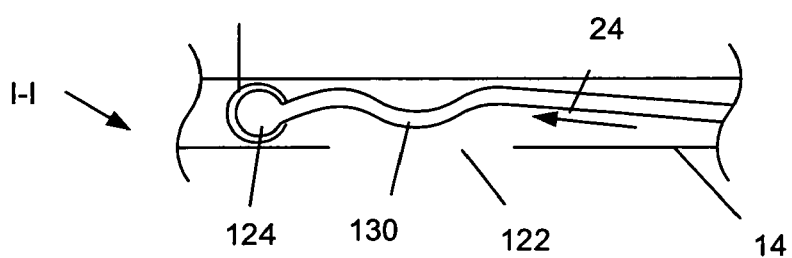

FIG. 30 illustrates that the luminal retainer can be preformed with a curvature 130. When the deployment force is applied, shown by arrow, the luminal retainer 24 can relax, if pre-stressed (e.g., heat-treated to a specific shape), and/or be forced into buckling into the anchor 14 across from the luminal retainer exit port 122. The luminal retainer 24 can then buckle and/or twist at the weakest point along the length, for example the curvature 130. The luminal retainer 24 can then exit through the luminal retainer exit port 122.

Figure 31:
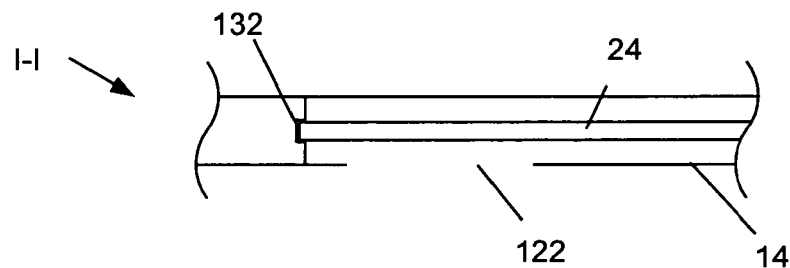
Figure 32:
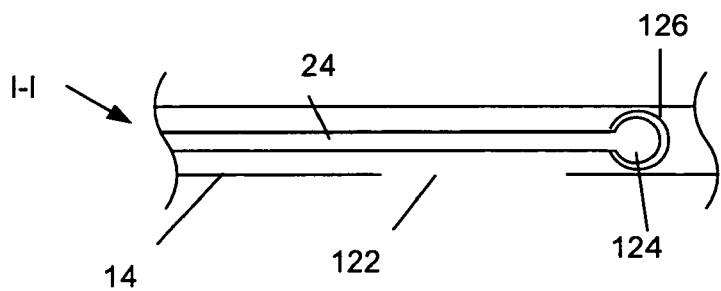

FIG. 31 illustrates that the luminal retainer 24 can be fixed to the anchor 14, for example at a fixation area 132 (e.g., via welding, gluing, snap fitting, etc.). FIG. 32 illustrates that the embodiments of the luminal retainer can be reversed in direction with respect to the remainder of the arteriotomy device 2.

Figure 33:
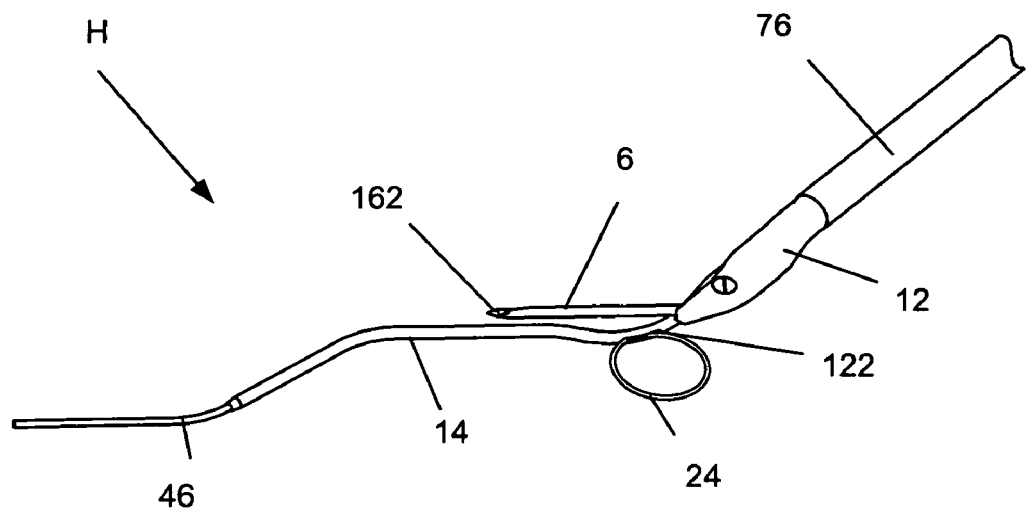
FIGS. 33 and 34 are a perspective and side view, respectively, of an embodiment of section H of FIG. 26.
Figure 34:
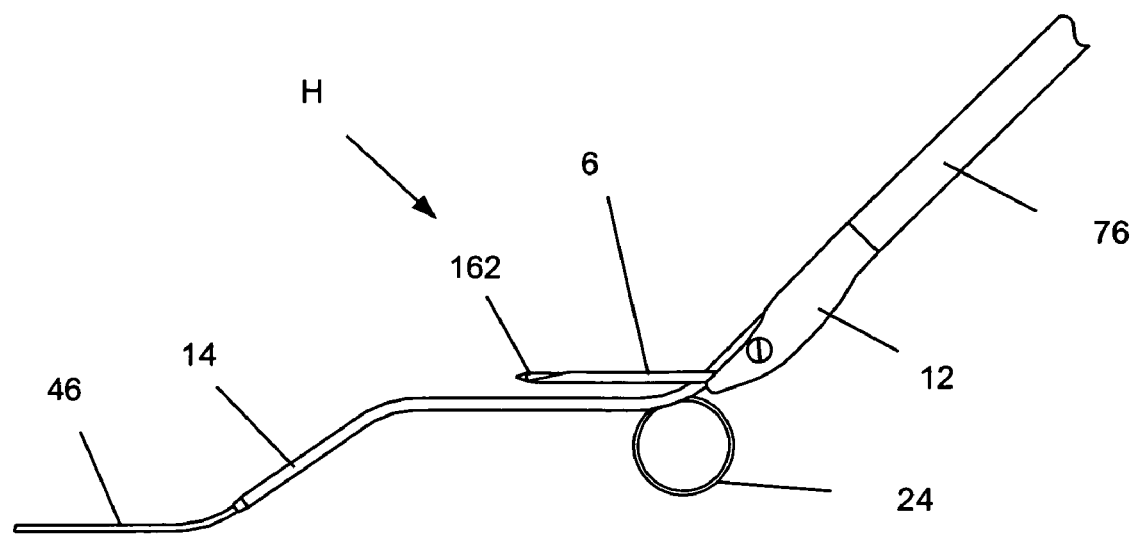

FIGS. 33 and 34 illustrate that the luminal retainer 24 can deploy as the loop or spiral. The luminal retainer 24 can deploy out of the luminal retainer exit port 122 on the anchor (as shown) and/or the delivery guide 12.

Figure 35:
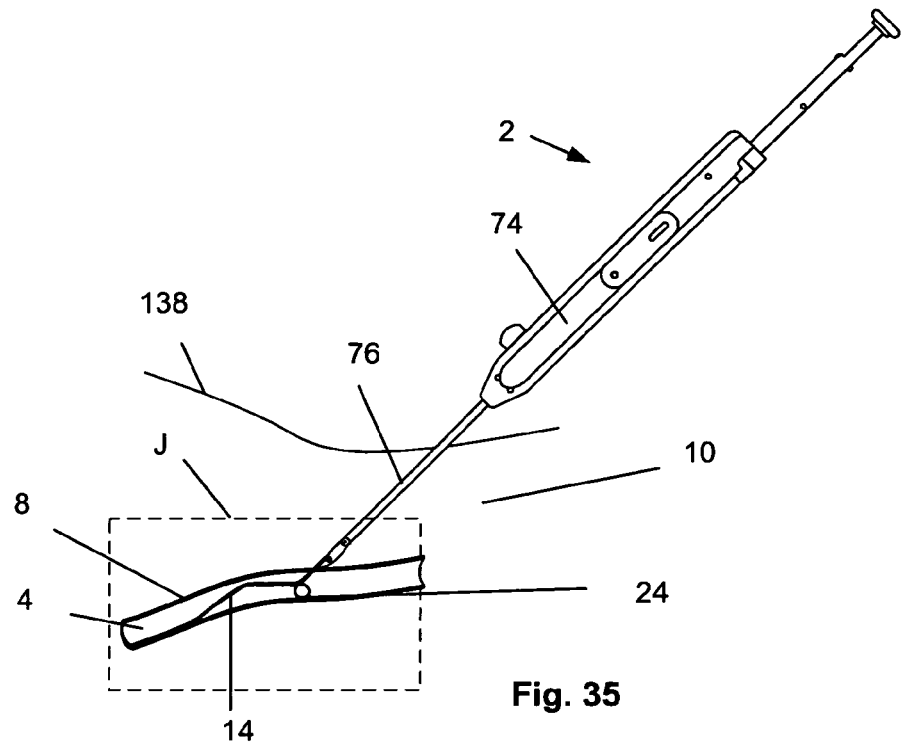
FIG. 35 illustrates an embodiment of a method of using the arteriotomy device in a cross-section of a lumen.
Figure 36:
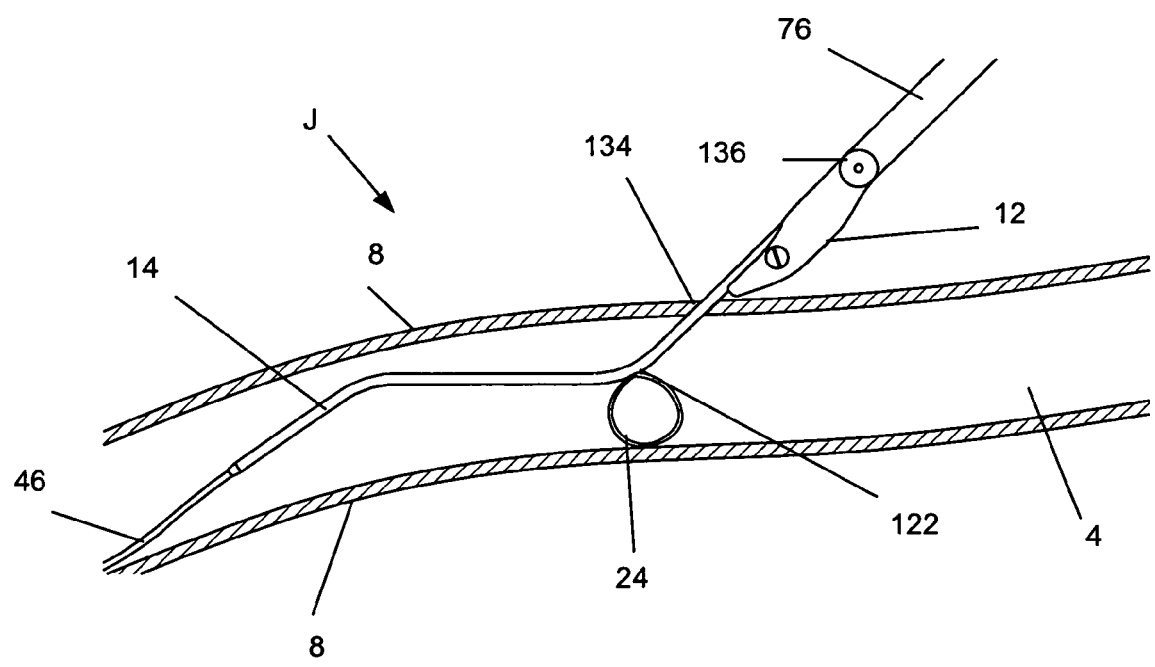
FIG. 36 is a close-up view of an embodiment of section J of FIG. 35.
Figure 37:
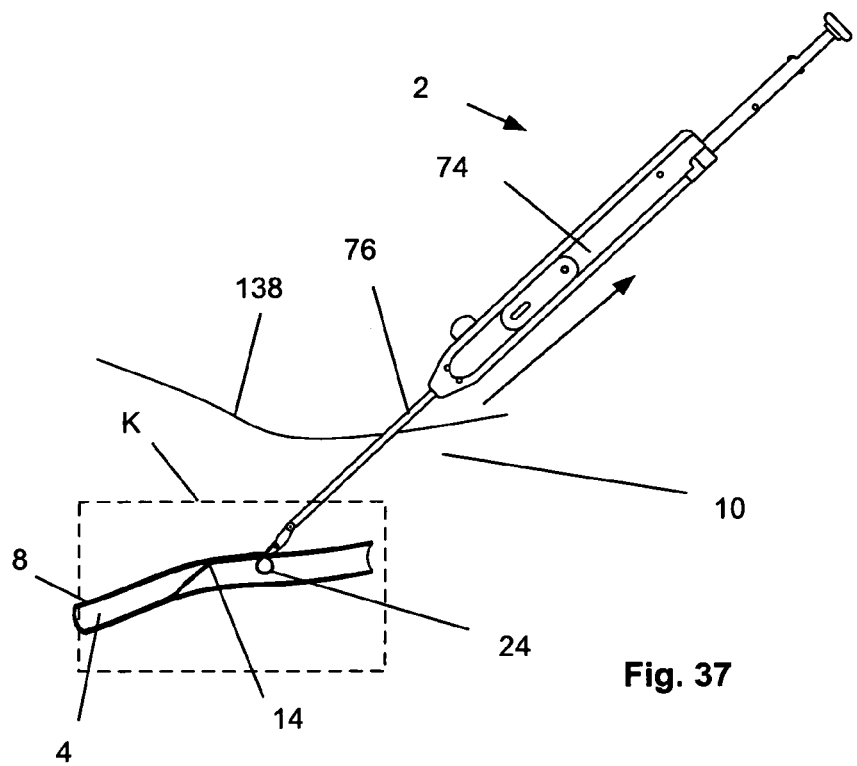
FIG. 37 illustrates an embodiment of a method of using an embodiment of the arteriotomy device of FIG. 35 in a cross-section of a lumen.
Figure 38:
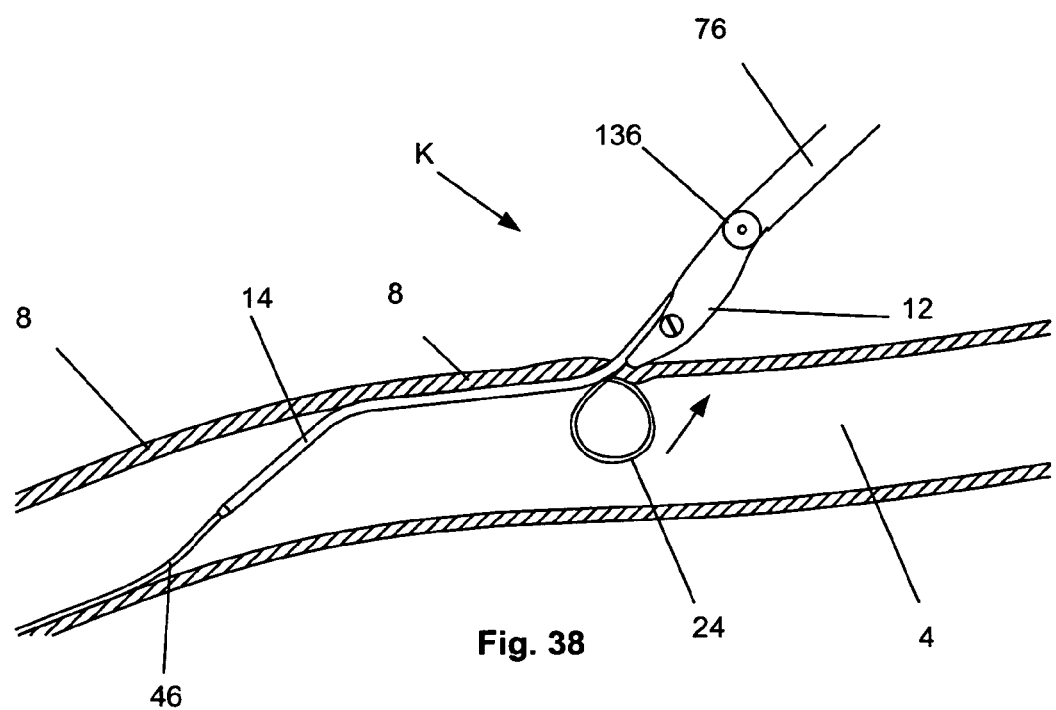
FIG. 38 is a close-up view of an embodiment of section K of FIG. 37.

FIGS. 35 and 36 illustrate that arteriotomy device 2 can be translated deep enough into the lumen 4 to contact the deployed luminal retainer 24 against the lumen wall 8 opposite from the arteriotomy 134. FIGS. 37 and 38 illustrate that the handle 74 can be translated, as shown by arrow in FIG. 37, away from the lumen 4. The luminal retainer 24 can be translated, as shown by arrow in FIG. 38, into the lumen wall 8 closest to the arteriotomy 134. The luminal retainer 24 can abut the lumen wall 8, for example, acting as the entry wall retainer 26. The delivery guide extension 76 can be rotatably attached to the delivery guide 12, for example by a hinge 136.

Figure 39:
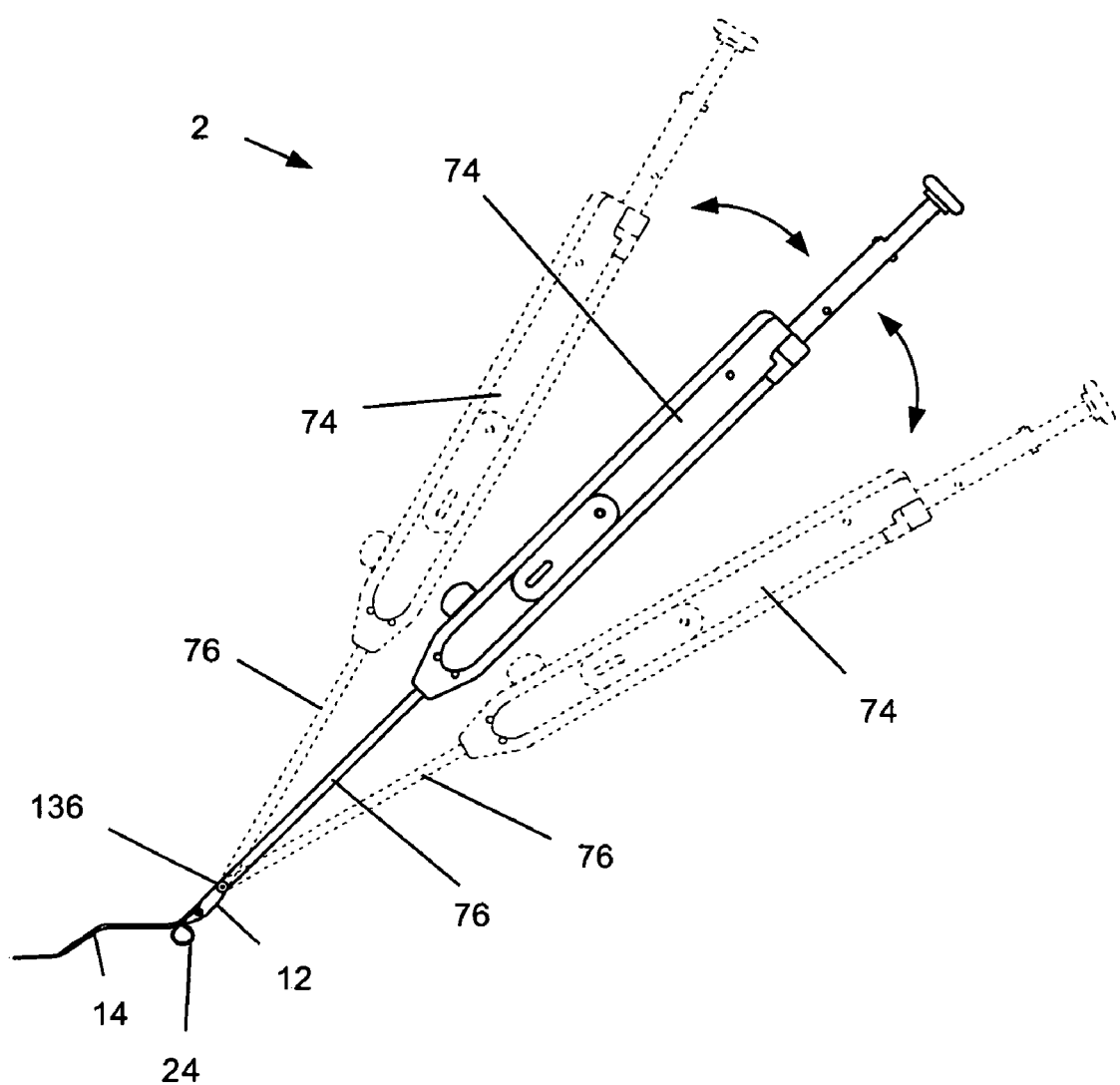
FIGS. 39 and 40 illustrate various methods of using the arteriotomy device.

FIG. 39 illustrates that the handle 74 and the delivery guide extension 76 can rotate around the hinge, as shown by arrows, with respect to the delivery guide 12, the anchor 14 and the luminal retainer 24. Rotated configurations of the handle 74 and the delivery guide extension are shown in phantom lines. The handle 74 and delivery guide extension 76 can be manipulated during use with a minimal impact on the delivery guide 12, the anchor 14 and the luminal retainer 24.

Figure 40:
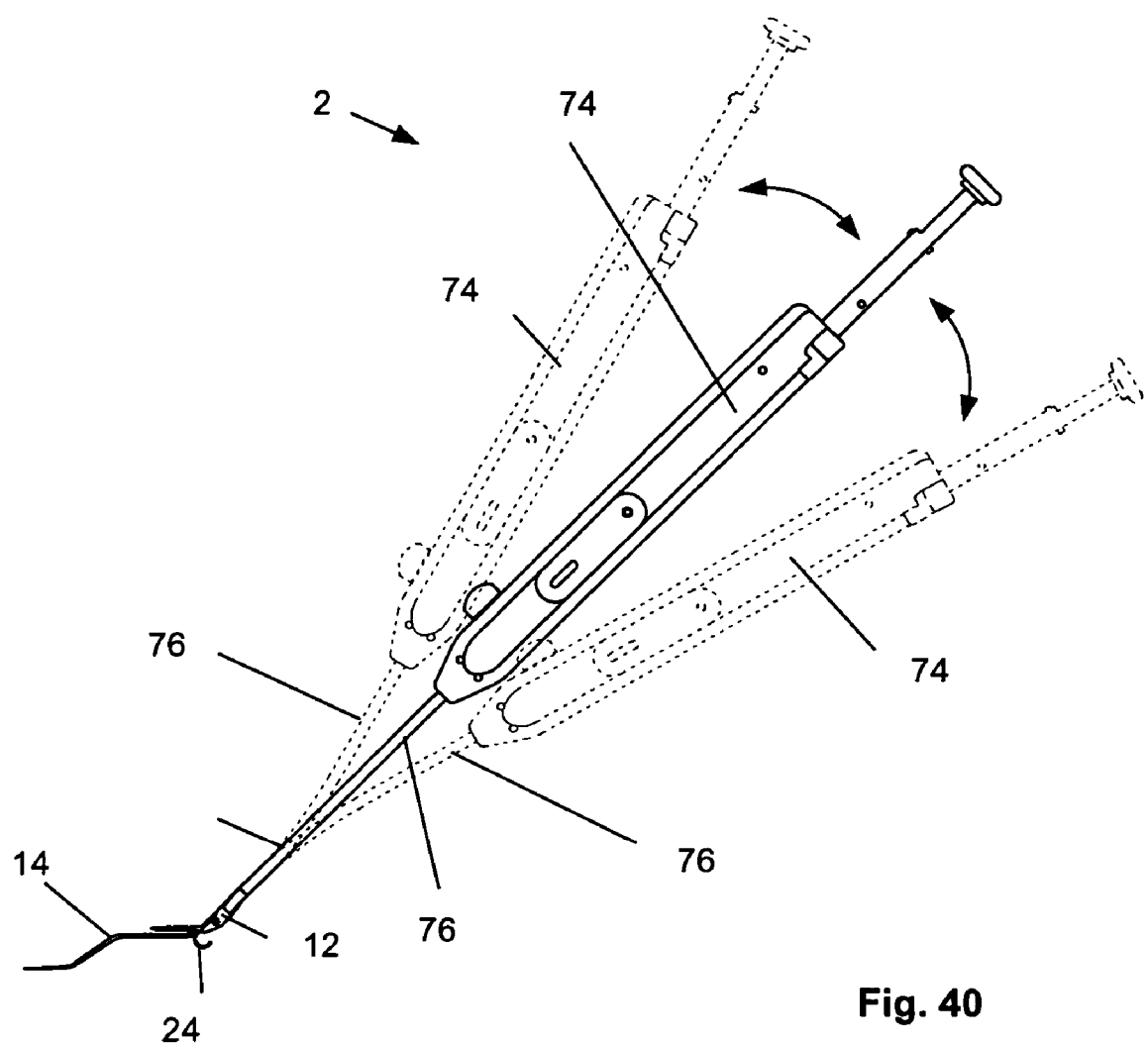

FIG. 40 illustrates that the delivery guide extension can be flexible. The handle 74 and the delivery guide extension 76 can rotate around the flexible delivery guide extension 76, as shown by arrows, with respect to the delivery guide 12, the anchor 14 and the luminal retainer 24. Rotated configurations of the handle 74 and the delivery guide extension are shown in phantom lines.

Figure 41:
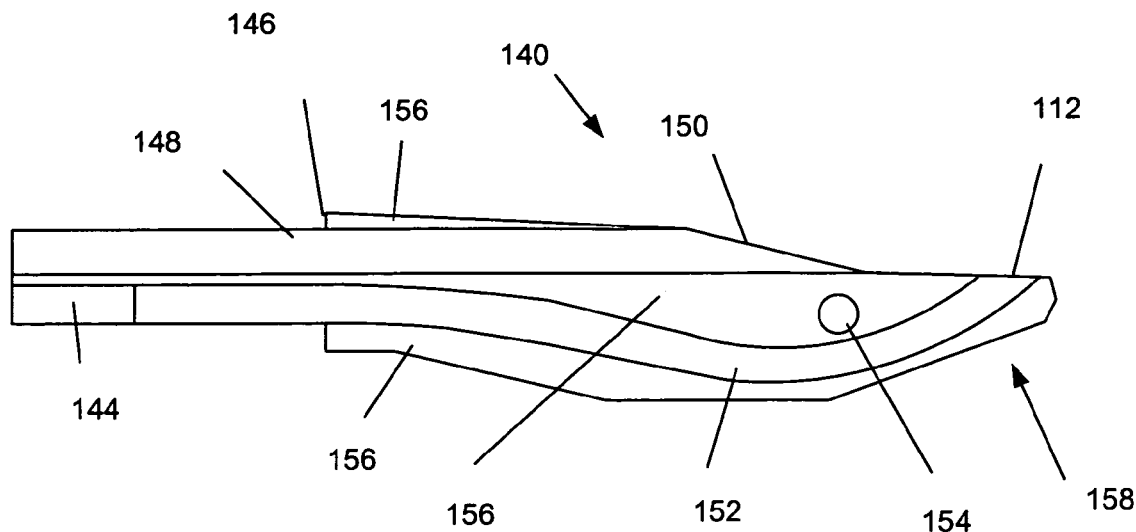
FIGS. 41 and 42 illustrate sectional views of an embodiment of the delivery guide.
Figure 42:
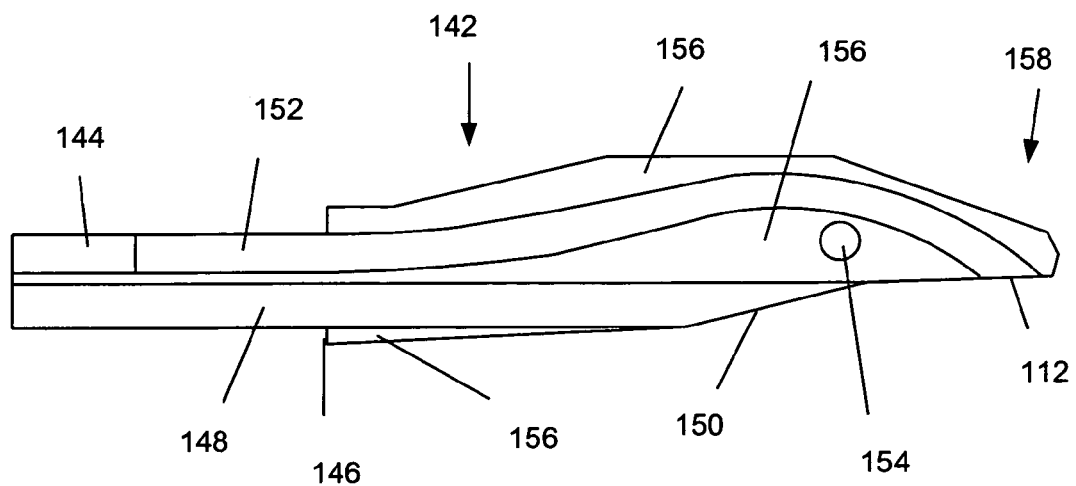

FIG. 41 illustrates a first longitudinal section 140 of the delivery guide 12. FIG. 42 illustrates a second longitudinal section 142 of the delivery guide 12. The first longitudinal section 140 can be a complete or substantial mirror image of the second longitudinal section 142.

An extension attachment 144 can be configured to fixedly attach to the delivery guide extension 76. The extension abutment 146 can be configured to abut against and/or fixedly attach to the delivery guide extension 76. The extension attachment 144 and/or extension abutment 146 can form fluid-tight and/or air-tight seals with the delivery guide extension 76.

The anchor lumen 148 can be configured to receive and deploy the anchor 14 out the anchor exit port 150. The introducer lumen 152 can be configured to receive and deploy the introduction device 6 out the introduction lumen exit port 112. The relative geometries of the anchor lumen 148, the introducer lumen 152, the anchor exit port 150, and the introduction lumen exit port 112 can be changed to alter the introduction angle 20, introduction run 38, introduction rise 40, and the geometry of the arteriotomy 134 including the geometries of the slopes 60 and flats 58 of the arteriotomy 134.

The delivery guide half attachments 154 can attach the first longitudinal section 140 to the second longitudinal section 142, for example by rotatably attaching to a screw. The seam surfaces 156 of the first longitudinal section 140 can form fluid-tight and/or air-tight seals with the seam surfaces 156 of the second longitudinal section 142. The delivery guide tip 158 can be sharpened, dulled, or otherwise configured to aid sharp or blunt dissection.

Figure 43:
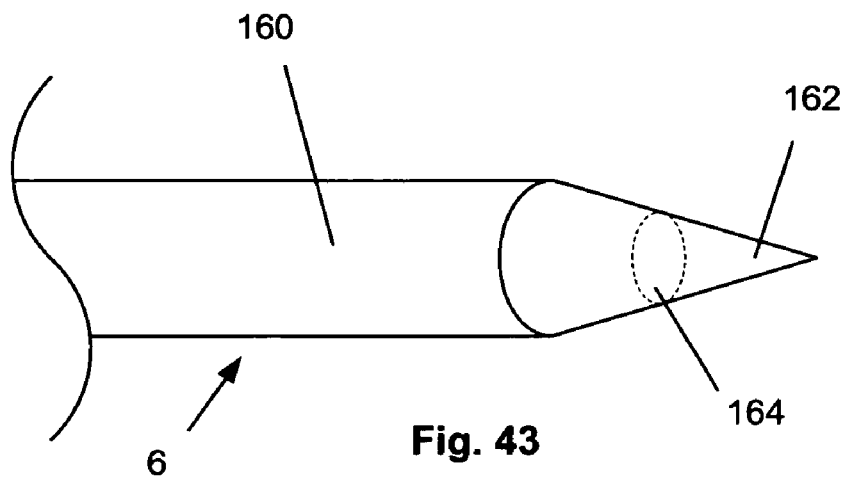
FIGS. 43 through 48 illustrate various embodiments of the introduction device.

FIGS. 43 through 46 illustrate solid introduction devices 6 that can each have an introduction device shaft 160 that can terminate in an introduction device tip 162. As shown in FIG. 43, the introduction device tip 162 can have a centered needle point. The introduction device tip 162 can have an introduction device tip cross-section 164. The introduction device tip cross-section 164 can be circular or square or combinations thereof. The introduction device tip can be curved (not shown).

Figure 44:
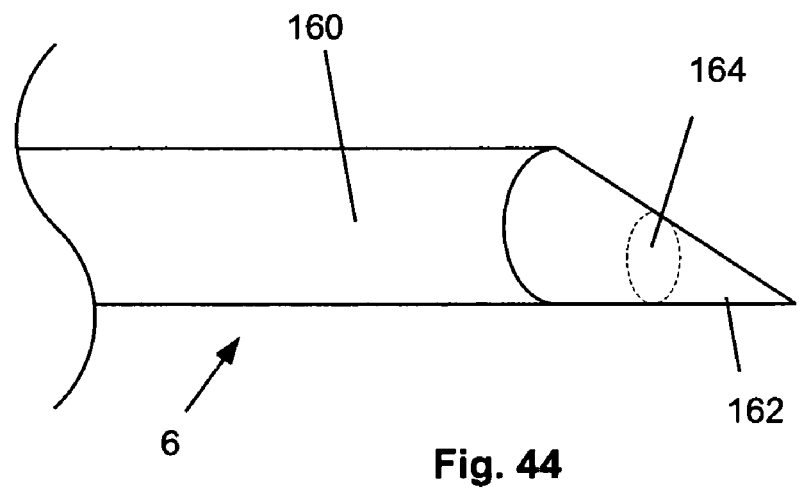

FIG. 44 illustrates that the introduction device tip 162 can have an off-center needle point. The introduction device tip cross-section 164 can be circular or square or combinations thereof. The introduction device 6 can be configured to have a flat side along the introduction device shaft 160 and along the introduction device tip 162.

FIG. 45 illustrates that the introduction device tip 162 can have a centered chisel point. The introduction device tip cross-section 164 can be oval, rectangular, elliptical, or a combination thereof.

FIG. 46 illustrates that the introduction device tip 162 can have a off-centered chisel point. The introduction device tip cross-section 164 can be oval, rectangular, elliptical, or a combination thereof. The introduction device 6 can be configured to have a flat side along the introduction device shaft 160 and along the introduction device tip 162.

FIGS. 47 through 53 illustrate hollow introduction devices 6 that can each have an introduction device shaft 160 that can terminate in an introduction device tip 162. The introduction device shaft 160 can have a hollow guide lumen 92 than can extend to the introduction device tip 162 or to the side of the introduction device shaft 160. The guide lumen 92 can terminate at a guide port 166. A guide (e.g., a guidewire or other tool) can be slidably attached to the introduction device 6 in the guide lumen 92. The guide lumen can have a guide shaft 168 that can terminate in a guide tip 170. The guide 172 can exit the introduction device at the guide port 166.

Figure 47:
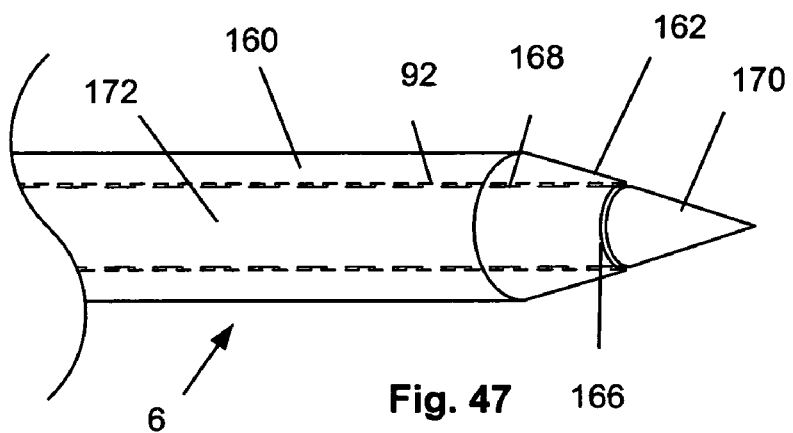

As shown in FIG. 47, the introduction device tip 162 can be a centered hollow needle point. The guide tip 170 can be a centered needle point. The guide tip 170 can be aligned with the introduction device tip to form a substantially smooth combined tip.

Figure 48:
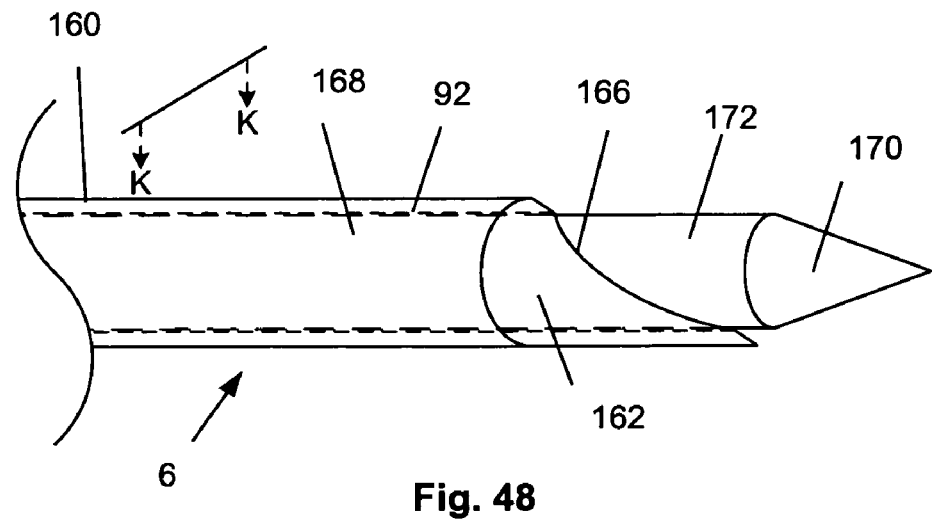

As shown in FIG. 48, the introduction device tip 162 can be an off-center hollow needle point. The guide tip 170 can be a centered needle point.

Figure 49:
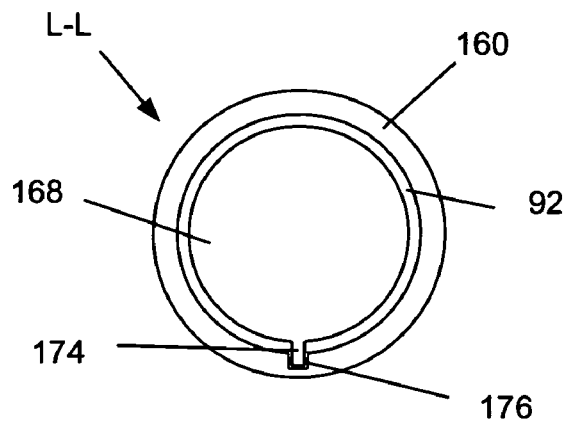
FIGS. 49 and 50 are various embodiments of cross-section K-K of FIG. 48.

FIG. 49 illustrates that the guide shaft 168 can have a key 174 and/or a slot 176 (not shown). The introduction device shaft 160 can have a slot 176 and/or a key 174 (not shown). The key 174 on the guide shaft 168 can slidably attach to the slot 176 in the introduction device shaft 160. The slidable attachment of the key 174 and slot 176 can prevent the guide shaft 168 from rotating about a longitudinal axis with respect to the introduction device shaft 160.

Figure 50:
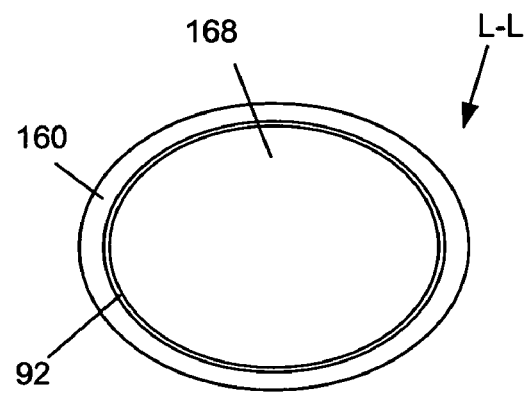

FIG. 50 illustrates that the guide lumen 92 and the guide shaft 168 can be oval. The oval configurations of the guide lumen 92 and the guide shaft 168 can prevent the guide shaft 168 from rotating about a longitudinal axis with respect to the introduction device shaft 160.

Figure 51:
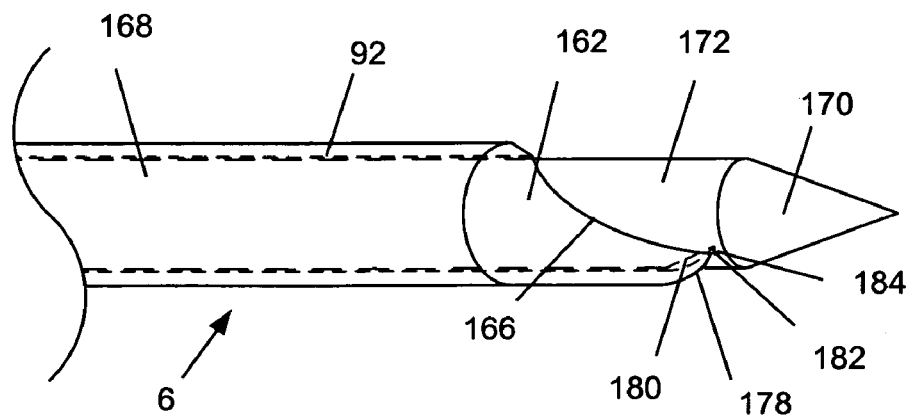
FIGS. 51 through 53 illustrate various embodiments of the introduction device.

FIG. 51 illustrates that the introduction device tip 162 can have a curved end 178. The curved end 178 can be configured to fit into a recess 180 in the guide 172. The recess 180 can have a hook 182. The curved end 178 can have a notch 184. The hook 182 can interference fit and/or snap fit the notch 184.

Figure 52:
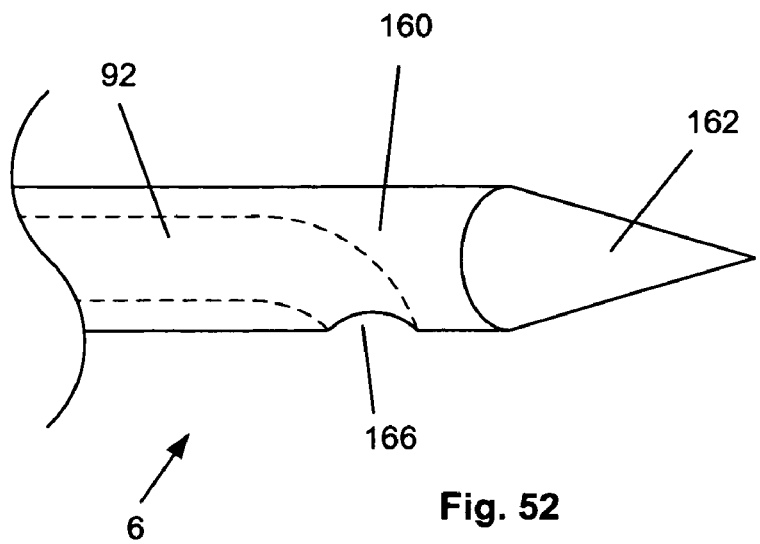

FIG. 52 illustrates that the guide lumen 92 can be curved. The guide lumen 92 can terminate at a guide port 166 in the side of the introduction device shaft 160.

Figure 53:
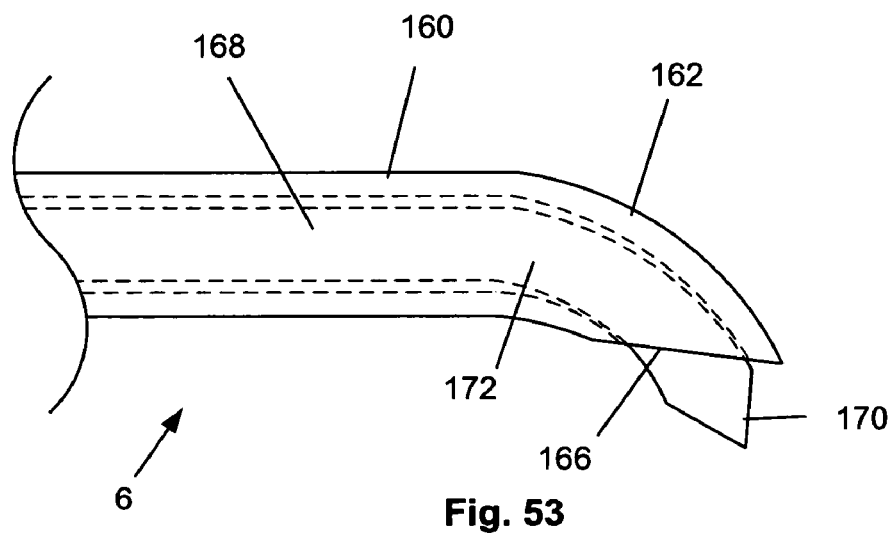

FIG. 53 illustrates that the introduction device tip 162 and/or the introduction device shaft (not shown) can be curved. The guide 172 or lengths of the guide 172 can be curved in a relaxed configuration. The guide 172 or lengths of the guide 172 can be curved in a stressed configuration due to the curvature of the introduction device 6.

Any of the introduction devices 6 shown in FIG. 43 through FIG. 46 can be hollowed and configured identically or similar to the introduction devices illustrated in FIG. 47 through FIG. 53. Any of the introduction devices 6 shown in FIG. 47 through FIG. 53 can have no guide lumen and be configured identically or similar to the introduction devices illustrated in FIG. 43 through FIG. 46.

The guides 172 and/or guide lumens 92 and/or introduction devices 6 can have a lubricious coating or be impregnated to elute a lubricious material.

Figure 54:
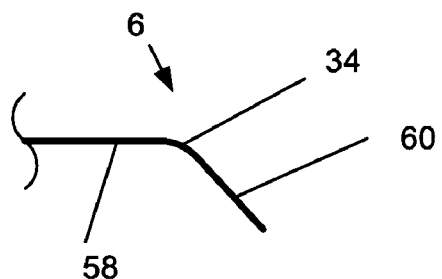
FIGS. 54 and 55 illustrate various embodiments of the introduction device in relaxed configurations.

FIG. 54 illustrates that the introduction device 6 can have a relaxed configuration having a flat 58 that can have a bend 34 at one end. A slope can extend from the bend 34. The relaxed configuration of the introduction device 6 can form the arteriotomy configuration, for example, as shown in FIGS. 7 and 9, during deployment of the introduction device 6 from the delivery guide 12.

Figure 55:
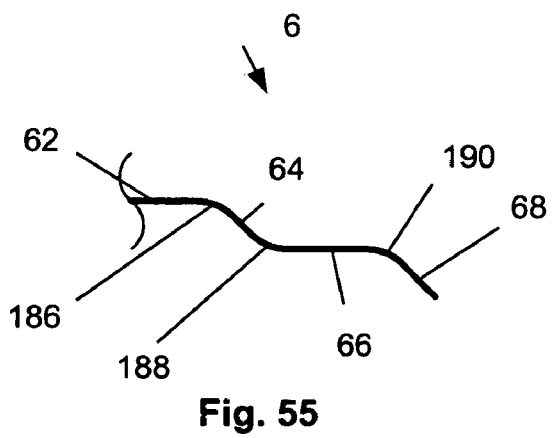

FIG. 55 illustrates that the introduction device 6 can have a relaxed configuration having a first flat 62 that can have a first bend 186 at one end. A first slope 64 can extend at a first end from the first bend 186. The first slope 64 can have at a second end a second bend 188. A second flat 66 can extend at a first end from the second bend 188. The second flat 66 can have at a second end a third bend 190. A second slope 68 can extend from the third bend 190. The relaxed configuration of the introduction device 6 can form the arteriotomy configuration, for example, as shown in FIGS. 8, 10 and 11, during deployment of the introduction device 6 from the delivery guide 12.

The introduction device 6, for example a hollow introduction device 6, can act as a pathway for a luminal tool, for example tools such as a guidewire 46, to be deployed into the lumen 4. The introduction device 6, for example a solid introduction device 6, can be removed from the second arteriotomy 28 and the luminal tool can be deployed through, for example, the introduction lumen exit port 112, and the second arteriotomy 28. The introduction device 6, or part thereof, can be the luminal tool, for example the guide 172. The introduction device 6 can be further deployed and used as a luminal tool after passing through the lumen wall 8.

The guide 172 can remain substantially in place after the arteriotomy device 2 is removed. A portion of the guide 172 can be outside the lumen 4 and another portion of the guide 172 can be inside the lumen 4. The guide proximal end can then be attached to additional devices and implants to guide the devices and implants into the lumen. The filler 70 can be added after additional procedures are completed and the guide 172 is removed, or before the guide 172 is removed, using the guide 172 to redeploy the arteriotomy device 2 back to the arteriotomy 134 to deliver the filler 70.

Method of Manufacture

The elements of the arteriotomy device 2, and those of any other devices and components disclosed herein, can be directly attached by, for example, melting, screwing, gluing, welding or use of an interference fit or pressure fit such as crimping, snapping, or combining methods thereof. The elements can be integrated, for example, molding, die cutting, laser cutting, electrical discharge machining (EDM) or stamping from a single piece or material. Any other methods can be used as known to those having ordinary skill in the art.

Integrated parts can be made from pre-formed resilient materials, for example resilient alloys (e.g., Nitinol, ELGILOY®) that are preformed and biased into the post-deployment shape and then compressed into the deployment shape as known to those having ordinary skill in the art.

Any elements of the arteriotomy device 2, and those of any other devices and components disclosed herein, including the supplemental closure devices, as a whole after assembly, can be coated by dip-coating, brush-coating or spray-coating methods known to one having ordinary skill in the art.

One example of a method used to coat a medical device for vascular use is provided in U.S. Pat. No. 6,358,556 by Ding et al. and hereby incorporated by reference in its entirety. Time release coating methods known to one having ordinary skill in the art can also be used to delay the release of an agent in the coating, for example the coatings on the supplemental closure devices.

Any elements herein can be covered with a fabric, for example polyester (e.g., DACRON® from E. I. du Pont de Nemours and Company, Wilmington, Del.), polypropylene, PTFE, ePTFE, nylon, extruded collagen, silicone or combinations thereof. Methods of covering an implantable device with fabric are known to those having ordinary skill in the art.

As shown in FIGS. 13, 41 and 42, the delivery guide 12 can be fixedly composited, for example with a weld, unitary construction (e.g., by casting), snap fitting components, a screw 192, or combinations thereof. The screw 192 can attach the delivery guide 12 to the delivery guide extension 76, for example by screwing through the delivery guide and/or by squeezing the delivery guide onto the delivery guide extension.

The radiopaque marks can be attached to the elements and/or coated on the surface of the elements and/or manufactured integrally in the elements.

The introduction device 6, guide 172, anchor 14, luminal retainer 24, entry wall retainer 26, any other elements, or combinations thereof can be heat set in a relaxed configuration using methods know to those having ordinary skill in the art.

It is apparent to one skilled in the art that various changes and modifications can be made to this disclosure, and equivalents employed, without departing from the spirit and scope of the invention. Elements shown with any embodiment are exemplary for the specific embodiment and can be used on other embodiments within this disclosure.

I claim:

1. A method for accessing a lumen of a vessel, the lumen defined by a vessel wall, the method comprising:
  a. advancing a first elongate member across the vessel wall to a deployed configuration wherein at least a portion of the first elongate member occupies the lumen, the first elongate member creating a first pathway through the vessel wall;
  b. using the deployed configuration of the first elongate member to mechanically enforce an introduction angle for advancing a second elongate member across at least a portion of the vessel wall;
  c. advancing the second elongate member across the vessel wall to a position wherein a second pathway is created through the vessel wall to the lumen; and
  d. delivering a filler into the second pathway, wherein the filler comprises a solid setting liquid.

2. The method of claim 1, wherein advancing the first elongate member comprises inserting an introduction device between an outer surface of the vessel wall and tissue surrounding the outer surface of the vessel wall.

3. The method of claim 2, wherein the tissue surrounding the outer surface of the vessel wall comprises adventitia.

4. The method of claim 1, wherein the first elongate member comprises an anchor, and wherein using the deployed configuration to mechanically enforce an introduction angle comprises using the anchor to stabilize the second elongate member with respect to the lumen.

5. The method of claim 4, wherein the second elongate member is advanced through the vessel wall while the anchor stabilizes the second elongate member with respect to the lumen.

6. The method of claim 1, wherein the second pathway is a self-sealing pathway.

7. The method of claim 1, wherein the filler comprises an epoxy.

8. The method of claim 1, further comprising advancing a third elongate member through the second elongate member.

9. A method for accessing a lumen of a vessel, the lumen defined by a vessel wall, the method comprising:
  a. advancing a first elongate member across the vessel wall to a deployed configuration wherein at least a portion of the first elongate member occupies the lumen, the first elongate member creating a first pathway through the vessel wall;
  b. using the deployed configuration of the first elongate member to mechanically enforce an introduction angle for advancing a second elongate member across at least a portion of the vessel wall;
  c. advancing the second elongate member across the vessel wall to a position wherein a second pathway is created through the vessel wall to the lumen; and
  d. applying pressure to the second pathway by delivering a filler adjacent to the second pathway.

10. The method of claim 9, wherein delivering filler comprises delivering filler into a portion of the second pathway located between an outer surface of the vessel wall and tissue surrounding the outer surface of the vessel wall.

11. The method of claim 9, wherein delivering filler comprises delivering filler in the vessel wall.

12. The method of claim 9, wherein delivering filler comprises delivering filler into tissue surrounding an outer surface of the vessel wall.

13. The method of claim 9, further comprising advancing a third elongate member through the second elongate member.

14. The method of claim 9, wherein the filler comprises a solid setting liquid.

15. The method of claim 14, wherein the filler comprises an epoxy.

* * * * *